United States Patent [19]

Suzuki et al.

[11] 4,337,256
[45] Jun. 29, 1982

[54] 1-PHENYL ISOQUINOLINE-5-ACETIC ACID COMPOUNDS AND ANALGESIC COMPOSITIONS THEREOF

[75] Inventors: Yasushi Suzuki, Yokohama; Kunio Tsukamoto, Tokyo; Nobuyoshi Minami, Yokohama; Yukio Hasegawa, Yamato; Michitaka Satoh; Norio Yamamoto, both of Kawasaki; Katsuhiko Miyasaka, Atsugi; Takashi Mikami, Tokyo; Satoshi Funakoshi, Kawasaki, all of Japan

[73] Assignee: Teikoku Hormone Manufacturing Co., Ltd., Tokyo, Japan

[21] Appl. No.: 107,613

[22] Filed: Dec. 27, 1979

[30] Foreign Application Priority Data

Dec. 27, 1978 [JP] Japan .................... 53/160026

[51] Int. Cl.³ .................... C07D 217/16; A61K 31/47
[52] U.S. Cl. .................... 424/258; 546/144; 546/147; 546/145
[58] Field of Search ............... 546/144, 145, 147, 146; 424/258

[56] References Cited

PUBLICATIONS

Beilstein, Handbuch der Org. Chemie, Band XX, Haupt., p. 82, Springer, Berlin (1935).
French et al., J. Med. Chem., vol. 73, pp. 1117–1118 (1970).
Walsh, J. Med. Chem., 21, pp. 582–585 (1978).

Primary Examiner—David B. Springer
Attorney, Agent, or Firm—Wenderoth, Lind & Ponack

[57] ABSTRACT

Novel isoquinoline derivatives of the general formula

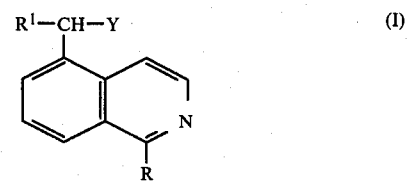

wherein
R represents a lower alkyl group, a lower cycloalkyl group, or a group of the formula

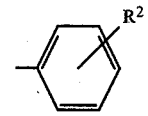

in which $R^2$ represents a hydrogen atom, a halogen atom, a methyl group, a trifluoromethyl group, a methoxy group, a methylamino group or a dimethylamino group;
$R^1$ represents a hydrogen atom or a lower alkyl group; and
Y represents a carboxyl group, a cyano group, a carbamoyl group, a lower alkoxycarbonyl group or a lower alkylaminocarbonyl group;

or a salt thereof; a process for the production thereof.

The above compound is useful as an anti-inflammatory and analgesic agent.

10 Claims, No Drawings

1-PHENYL ISOQUINOLINE-5-ACETIC ACID COMPOUNDS AND ANALGESIC COMPOSITIONS THEREOF

This invention relates to novel isoquinoline derivatives. More specifically, this invention relates to novel isoquinoline derivatives having a lower alkyl group, a lower cycloalkyl group or a phenyl group at the 1-position of the isoquinoline nucleus and a carboxyalkyl or cyanoalkyl group or a group derived therefrom at the 5-position of the isoquinoline nucleus, a process for producing these isoquinoline derivatives and to use of these derivatives as anti-inflammatory and analgesic agents.

It was reported very recently that 1-(4-chlorophenyl)-3-carbamoylmethyl isoquinoline of the following formula

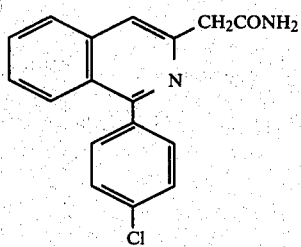

having a substituted phenyl group at the 1-position and a carbamoylmethyl group at the 3-position has anti-inflammatory and analgesic activities [see David A. Walsh et al., Journal of Medicinal Chemistry, 1978, Vol. 21, No. 6, pages 582–585].

As novel isoquinoline derivatives having very high anti-inflammatory and analgesic activities, the present invention provides compounds of the following general formula

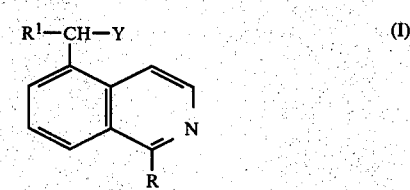

wherein

R represents a lower alkyl group, a lower cycloalkyl group, or a group of the formula

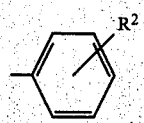

in which $R^2$ represents a hydrogen atom, a halogen atom, a methyl group, a trifluoromethyl group, a methoxy group, a methylamino group or a dimethylamino group;

$R^1$ represents a hydrogen atom or a lower alkyl group; and

Y represents a carboxyl group, a cyano group, a carbamoyl group, a lower alkoxycarbonyl group or a lower alkylaminocarbonyl group; and the salts thereof.

In the present application, the term "lower" means that groups or compounds qualified by this term contain not more than 6 carbon atoms.

The "lower alkyl group" may be an alkyl group in a straight or branched chain for example, methyl, ethyl, n-propyl, isopropyl, n-butyl, isobutyl, sec-butyl, and tert-butyl. A methyl group is preferred as the lower alkyl group represented by $R^1$. Suitable lower alkyl groups for R are lower alkyl groups in branched chains, especially an isopropyl group.

The "lower cycloalkyl group" represented by R may be cyclopropyl, cyclobutyl, cyclopentyl and cyclohexyl. Cyclopentyl and cyclohexyl groups are preferred, and from the viewpoint of pharmacological action, the cyclohexyl group is most preferred.

In the unsubstituted or substituted phenyl group

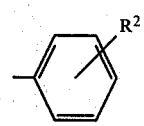

represented by R, the substituent $R^2$ on the benzene ring may be located at any of the ortho-, meta- and para-positions. Desirably, it is present at the para-position. As the substituent $R^2$, hydrogen, halogen (especially, Cl, Br and F), methyl, and dimethylamino are especially suitable.

Examples of the "lower alkoxycarbonyl group" are methoxycarbonyl, ethoxycarbonyl, n-propoxycarbonyl, isopropoxycarbonyl, n-butoxycarbonyl, and t-butoxycarbonyl group. Of these, methoxycarbonyl and ethoxycarbonyl are preferred.

The "lower alkylaminocarbonyl group" is a monovalent group which can be represented by the formula —CONH—(lower alkyl group), and may, for example, be methylaminocarbonyl, ethylaminocarbonyl, n-propylaminocarbonyl, isopropylaminocarbonyl, and n-butylaminocarbonyl. The methylamino group is preferred.

In general formula (I), the "halogen atom" may be any of fluorine, chlorine, bromine and iodine atoms, and fluorine, chlorine and bromine atoms are preferred.

Among the compounds of formula (I) provided by this invention, preferred groups of the compounds are as follows:

(i) Compounds of formula (I) in which R represents as isopropyl group, a cyclopentyl group, a cyclohexyl group, or a group of the formula

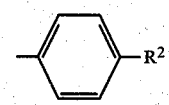

wherein $R^2$ is as defined above.

(ii) Compounds of formula (I) in which R is a group of the formula

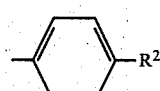

and $R^2$ represents a hydrogen atom, a chlorine atom, a bromine atom, a fluorine atom, a methyl group or a dimethylamino group.

(iii) Compounds of formula (I) in which $R^1$ represents a hydrogen atom or a methyl group, especially hydrogen.

(iv) Compounds of formula (I) in which Y represents a carboxyl or cyano group.

An especially preferred group of the compounds of this invention includes isoquinoline derivatives of the following formula

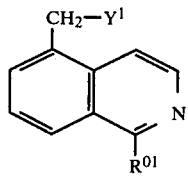
(I-3)

wherein $R^{01}$ represents an isopropyl group, a cyclopentyl group, a cyclohexyl group or a group of the formula

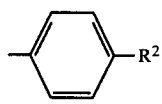

in which $R^2$ is as defined above, and $Y^1$ represents a carboxyl or cyano group;
and the salts thereof.

Compounds of formula (I) in which Y is a carboxyl group are especially important is this invention.

Typical examples of the compounds of general formula (I) are shown below.

1-phenylisoquinoline-5-acetic acid,
1-(4-fluorophenyl)isoquinoline-5-acetic acid,
1-(4-chlorophenyl)isoquinoline-5-acetic acid,
1-(4-bromophenyl)isoquinoline-5-acetic acid,
1-(4-methoxyphenyl)isoquinoline-5-acetic acid,
1-(4-methylphenyl)isoquinoline-5-acetic acid,
1-(4-methylaminophenyl)isoquinoline-5-acetic acid,
1-(4-dimethylaminophenyl)isoquinoline-5-acetic acid,
1-(4-trifluoromethylphenyl)isoquinoline-5-acetic acid,
1-(2-chlorophenyl)isoquinoline-5-acetic acid,
1-(2-bromophenyl)isoquinoline-5-acetic acid,
1-(3-bromophenyl)isoquinoline-5-acetic acid,
1-(2-methylaminophenyl)isoquinoline-5-acetic acid,
1-(3-methylaminophenyl)isoquinoline-5-aetic acid,
1-(2-dimethylaminophenyl)isoquinoline-5-acetic acid,
1-(3-dimethylaminophenyl)isoquinoline-5-acetic acid,
1-(2-methylphenyl)isoquinoline-5-acetic acid,
1-(3-trifluoromethylphenyl)isoquinoline-5-acetic acid,
1-ethylisoquinoline-5-acetic acid,
1-n-propylisoquinoline-5-acetic acid,
1-isopropylisoquinoline-5-acetic acid,
1-n-butylisoquinoline-5-acetic acid,
1-isobutylisoquinoline-5-acetic acid,
1-sec-butylisoquinoline-5-acetic acid,
1-tert-butylisoquinoline-5-acetic acid,
1-isopentylisoquinoline-5-acetic acid,
1-(1-methylbutyl)isoquinoline-5-acetic acid,
1-(1-ethylpropyl)isoquinoline-5-acetic acid,
1-n-hexylisoquinoline-5-acetic acid,
1-cyclopropylisoquinoline-5-acetic acid,
1-cyclobutylisoquinoline-5-acetic acid,
1-cyclopentylisoquinoline-5-acetic acid,
1-cyclohexylisoquinoline-5-acetic acid,
2-[1-(4-fluorophenyl)isoquinolin-5-yl]propionic acid,
2-[1-(4-chlorophenyl)isoquinolin-5-yl]propionic acid,
2-[1-(2-bromophenyl)isoquinolin-5-yl]propionic acid,
2-[1-(4-bromophenyl)isoquinolin-5-yl]propionic acid,
2-[1-(2-methylaminophenyl)isoquinolin-5-yl]-propionic acid,
2-[1-(4-methylaminophenyl)isoquinolin-5-yl]-propionic acid,
2-[1-(2-dimethylaminophenyl)isoquinolin-5-yl]-propionic acid,
2-[1-(3-dimethylaminophenyl)isoquinolin-5-yl]-propionic acid,
2-[1-(4-dimethylaminophenyl)isoquinolin-5-yl]-propionic acid,
2-[1-(4-methylphenyl)isoquinolin-5-yl]propionic acid,
2-[1-(4-methoxyphenyl)isoquinolin-5-yl]propionic acid,
2-(1-isopropylisoquinolin-5-yl)propionic acid,
2-(1-isobutylisoquinolin-5-yl)propionic acid,
2-(1-sec-butylisoquinolin-5-yl)propionic acid,
2-(1-cyclohexylisoquinolin-5-yl)propionic acid,
2-[1-(4-bromophenyl)isoquinolin-5-yl]butyric acid,
2-[1-(4-dimethylaminophenyl)isoquinolin-5-yl]-butyric acid,
methyl 1-(4-chlorophenyl)isoquinoline-5-acetate,
methyl 1-(4-bromophenyl)isoquinoline-5-acetate,
ethyl 1-(4-dimethylaminophenyl)isoquinoline-5-acetate,
ethyl 1-(4-methylphenyl)isoquinoline-5-acetate,
ethyl 1-cyclohexylisoquinoline-5-acetate,
1-(4-chlorophenyl)isoquinoline-5-acetamide,
1-(4-dimethylaminophenyl)isoquinoline-5-acetamide,
1-cyclohexylisoquinoline-5-acetamide,
1-(4-bromophenyl)isoquinoline-5-acetic acid methylamide,
1-(4-methylphenyl)isoquinoline-5-acetic acid methylamide,
1-(4-chlorophenyl)isoquinoline-5-acetonitrile,
1-(4-bromophenyl)isoquinoline-5-acetonitrile,
1-(4-methylaminophenyl)isoquinoline-5-acetonitrile,
1-(2-dimethylaminophenyl)isoquinoline-5-acetonitrile,
1-(4-dimethylaminophenyl)isoquinoline-5-acetonitrile,
1-(4-methylaminophenyl)isoquinoline-5-acetonitrile,
2-[1-(4-bromophenyl)isoquinolin-5-yl]propionitrile,
2-[1-(4-methylaminophenyl)isoquinolin-5-yl]-propionitrile, and
2-[1-(4-dimethylaminophenyl)isoquinolin-5-yl]-propionitrile.

Among these compounds, the following compounds are pharmacologically interesting.

1-(4-Chlorophenyl)isoquinoline-5-acetic acid,
1-(4-bromophenyl)isoquinoline-5-acetic acid,
1-(4-methylphenyl)isoquinoline-5-acetic acid,
1-(4-dimethylaminophenyl)isoquinoline-5-acetic acid, and
1-cyclohexylisoquinoline-5-acetic acid.

When Y represents a carboxyl group in the compounds of formula (I), the carboxyl group may form a salt. Examples of such salts include salts with inorganic bases such as sodium, potassium, lithium, calcium, magnesium, aluminum and ammonium salts, and salts with organic bases such as diethylamine, triethylamine, pyrrolidine, piperidine, morpholine, pyridine, brucine, and morphine. Pharmaceutically acceptable salts such as sodium, potassium and aluminum salts are preferred.

Since the compounds of formula (I) is basic owing to the N atom in the isoquinoline skeleton, they can form acid addition salts and quaternary salts. Examples of the acid addition salts include inorganic acid salts such as hydrochlorides, sulfates and phosphates, and organic acid salts such as acetates and propionates. Examples of the quaternary salts include salts with alkyl halides such as methyl iodide, methyl bromide, methyl chloride, ethyl iodide, ethyl bromide, and ethyl chloride. If these, pharmaceutically acceptable salts, for example, acid addition salts such as hydrochlorides, phosphates and quaternary salts such as methyl bromides are preferred.

The compounds of formula (I) of this invention can be produced by various methods. For example, the compounds of formula (I) can be produced in accordance with Synthetic Route I or II in the following Reaction Scheme A, irrespective of the type of group R. Compounds of formula (I) in which R represents a lower alkyl or lower cycloalkyl group can also be produced in accordance with Synthetic Route III of the following Reactions Scheme A. Compounds of formula (I) in which R is the group

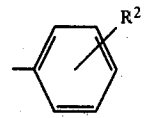

wherein $R^2$ is any of the groups defined above except methyl can also be produced in accordance with Synthetic Route IV in Reaction Scheme A.

Compounds of formula (I) in which R is the group

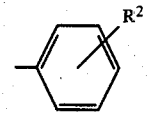

wherein $R^2$ represents a methylamino or dimethylamino group can also be produced by reducing compounds of the following formula

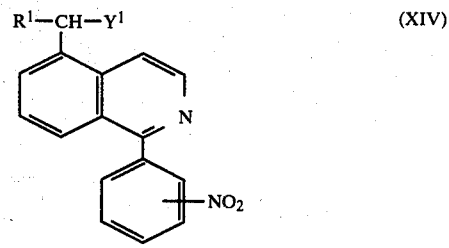

(XIV)

wherein $R^1$ and $Y^1$ are as defined above, produced from the corresponding starting materials in accordance with Synthetic Route I, II or IV, thereby converting the nitro group to an amino group, and then methylating the amino group.

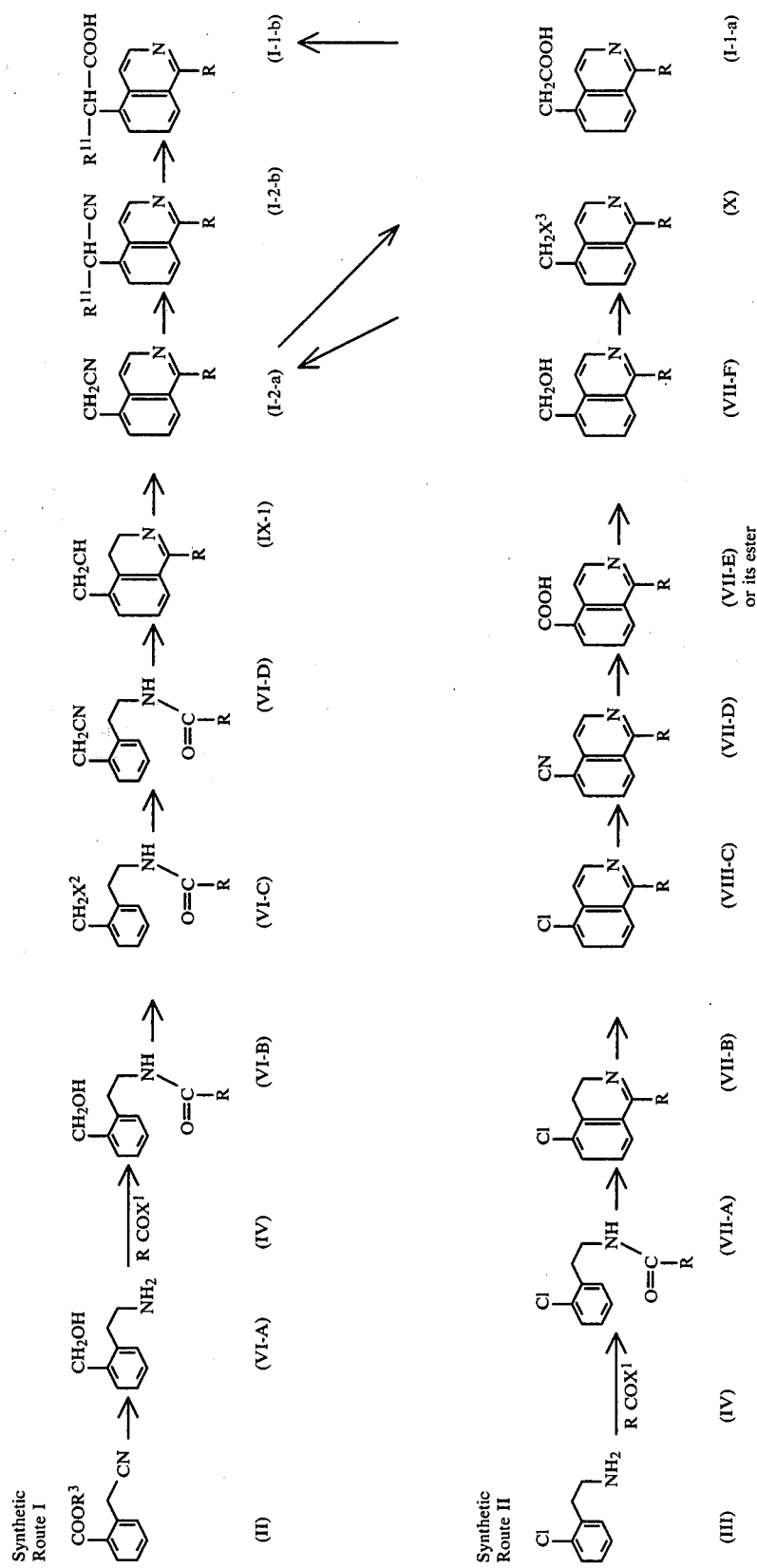

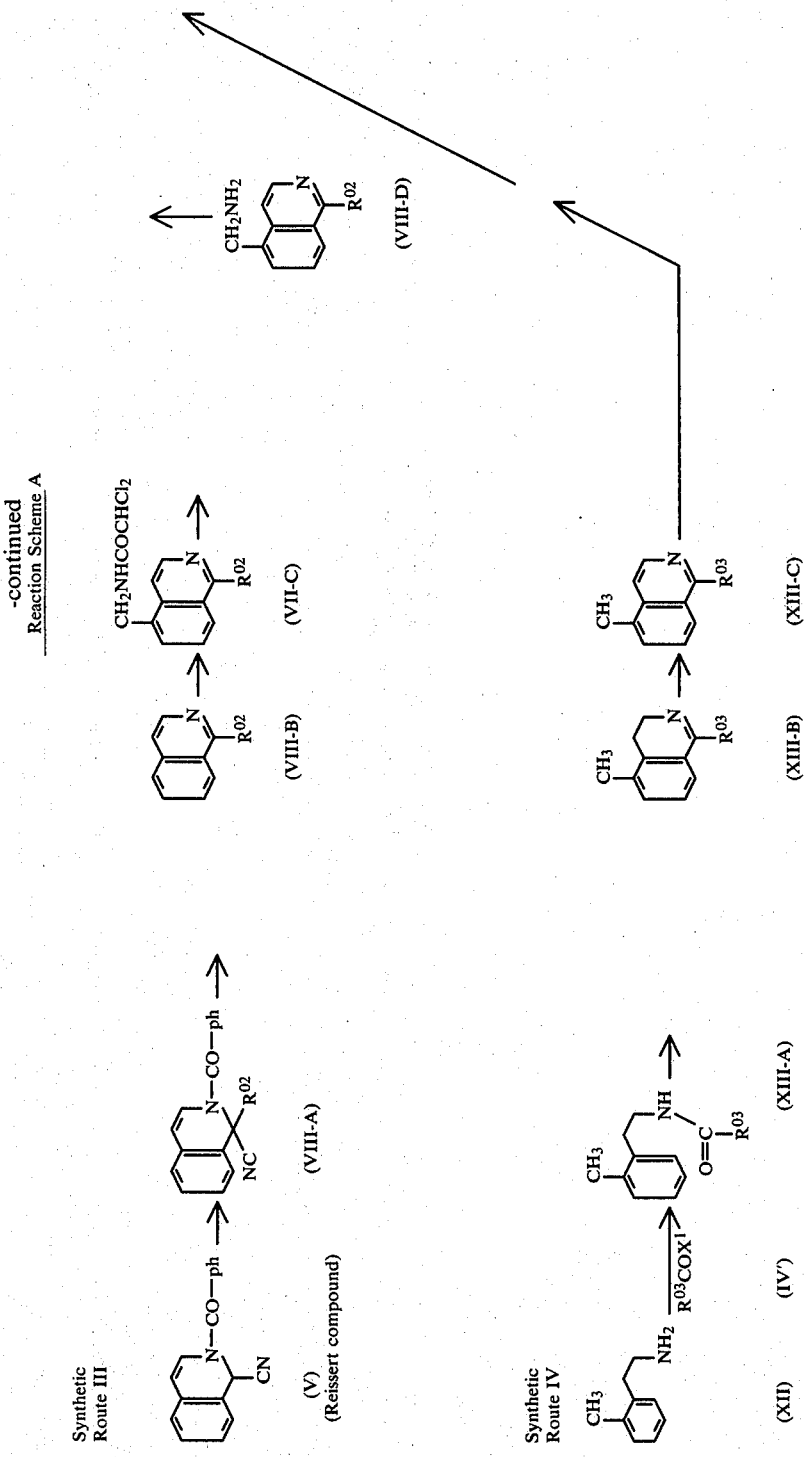

In the above formulae, R is as defined above, and $R^{11}$ represents a lower alkyl group, $R^3$ represents a lower alkyl group, and $X^1$, $X^2$ and $X^3$ each represent a halogen atom, $R^{02}$ represents a lower alkyl group or a lower cycloalkyl group, and $R^{03}$ represents the group

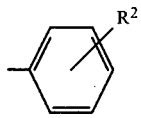

in which $R^2$ represents any of the groups defined above except a methyl group.

Synthetic Route I

According to Synthetic Route I, the 2-cyanomethylbenzoic acid ester (especially the methyl ester) of formula (II) is reduced to the compound of formula (VI-A). The reduction can be carried out by using a complex metal hydride such as lithium aluminum hydride, or dihydrobis(2-methoxyethoxy)aluminum sodium. As the solvent, inert organic solvent can be used, for example, ethers such as tetrahydrofuran, ethyl ether, dioxane and dimethoxyethane; aromatic hydrocarbons such as benzene, toluene and xylene; or mixtures of these organic solvents. The reducing reaction can be performed usually at a temperature of from room temperature to the refluxing temperature of the reaction mixture, preferably about 25° C. to about 60° C.

The resulting compound of formula (VI-A) is then amidated with an acyl halide of formula (IV). This reaction may be carried out usually in an inert organic solvent at room temperature to an elevated temperature, preferably about 15° C. to about 100° C. Examples of the inert organic solvent are halogenated hydrocarbons such as dichloromethane, chloroform and carbon tetrachloride; aromatic hydrocarbons such as benzene, toluene and xylene; organic bases such as triethylamine, dimethylaniline and pyridine; or mixtures of these. The ratio of the compound of formula (VI-A) to the acyl halide of formula (IV) is not particularly restricted. Generally, the compound of formula (IV) is added in an amount of 1 to 10 moles, preferably 1.1 to 2 moles, per mole of the compound of formula (VI-A).

Depending upon the reaction conditions in the aforesaid acylation reaction, the hydroxymethyl group ($-CH_2OH$) at the 2-position of the compound of formula (VI-A) may be simultaneously acylated to afford the corresponding compound of formula (VI-B) in which an acyloxymethyl group ($-CH_2OCOR$) is located at the 2-position. This compound can be converted to the compound of formula (VI-B) by hydrolyzing it under mild conditions.

The resulting compound of formula (VI-B) can be subsequently converted to the compound of formula (VI-C) by halogenation. The halogenation may be carried out by treating the compound of formula (VI-B) with a halogenating agent in the absence of a solvent or in the presence of a suitable solvent such as water, dichloromethane, chloroform, carbon tetrachloride, benzene, toluene or xylene. Useful halogenating agents include hydrogen chloride, thionyl chloride, phosphorus trichloride, phosphorus pentachloride, phosphorus oxychloride, hydrogen bromide, thionyl bromide, phosphorus tribromide, and phosphorus oxybromide. The halogenating agent can be used in an amount of generally at least 1 equivalent, preferably 1.1 to 10 equivalent, per mole of the compounds of formula (VI-B). Advantageously, the halogenation is carried out generally at room temperature to the refluxing temperature of the reaction mixture for about 1 to about 10 hours, preferably about 20° C. to about 150° C.

Thus, the compound of formula (VI-C) is obtained. Cyanidation of this compound affords the compound of formula (VI-D). The cyanidation can be achieved by treating the compound of formula (VI-C) with a suitable cyanidation agent usually in an inert organic solvent such as dimethylsulfoxide, dimethylformamide, ethanol, methanol and hydrous ethanol. Useful cyanidation agents include, for example, sodium cyanide, potassium cyanide and copper cyanide. Sodium cyanide is preferred. The amount of the cyanidation agent is usually at least 1 equivalent, preferably 1.1 to 2 equivalents, per mole of the compound of formula (VI-C).

The reaction temperature in the cyanidation is not critical, and can be varied over a wide range. Generally, it is preferable to carry out the reaction at a temperature of from about 0° C. to about 200° C., preferably room temperature to the refluxing temperature of the reaction mixture.

The compound of formula (VI-D) is then dehydrocyclized. This dehydrocyclization is a so-called Bishler-Napieralski reaction which can be carried out usually in the presence of a condensing agent at a temperature of at least about 50° C., preferably about 140° C. to about 250° C. Useful condensing agents include, for example, phosphorus oxychloride, phosphorus oxybromide, sulfuric acid, phosphoric acid, phosphorus pentoxide and polyphosphoric acid. Use of phosphorus oxychloride and phosphorus pentoxide is advantageous. The condensing agent is used desirably in an amount of at least 1 equivalent, preferably 2 to 10 equivalents, per mole of the compound of formula (VI-D).

The dehydrocyclization reaction can be carried out in the absence of a solvent. As required, however, it may be carried out in a suitable inert organic solvent such as benzene, toluene and xylene.

The compound of formula (IX-1) obtained by the dehydrocyclization can be converted to the compound of formula (I-2-a) by dehydrogenation. The dehydrogenation reaction can be performed by treating the compound of formula (IX-1) with a dehydrogenating agent in the absence of a solvent or in the presence of a suitable inert solvent, for example, hydrocarbons such as tetralin, benzene, toluene, xylene and mesitylene; water; acetic acid; or alcohols such as t-butanol or s-amyl alcohol. Examples of the dehydrogenating agent that can be used include diphenyl disulfide, 2,3-dichloro-5,6-dicyanobenzoquinone, tetrachloro-1,4-benzoquinone, sulfur, selenium, chromic acid, active manganese dioxide, and potassium permanganate. Of these, diphenyl disulfide is preferred. The amount of the dehydrogenating agent, which differs depending upon its type, is at least 1 equivalent, preferably 1.1 to 10 equivalents, per mole of the compound of formula (IX-1).

The reaction temperature is not critical, and can be varied depending upon the type of the dehydrogenating agent. Generally, it is about 0° C. to about 300° C., preferably room temperature to about 210° C. The dehydrogenating reaction can be terminated in about 0.5 to 30 hours under the aforesaid conditions.

The compound of formula (I-2-a) so obtained can be separated from the reaction mixture, and/or, purified, by methods known per se such as filtration, centrifugal separation, extraction, recrystallization, or chromatography. The compound of formula (I-2-a) itself has anti-inflammatory and analgesic activities and may be used as a medicine. By hydrolyzing it, it can be converted to a compound of formula (I-1-a) having higher anti-inflammatory and analgesic activities.

The hydrolysis of the compound of formula (I-2-a) can be carried out by using an aqueous solution of an alkali or an aqueous solution of an acid in the absence of solvent or in the presence of a water-miscible organic solvent, for example alcohols such as methanol, ethanol, and Cellosolve, ketones such as acetone or methyl ethyl ketone, ethers such as tetrahydrofuran, dimethoxyethane and dioxane, or dimethylsulfoxide.

Alkalies which can be used for the hydrolysis include alkali metal hydroxides or alkaline earth metal hydroxides such as sodium hydroxide, potassium hydroxide and barium hydroxide, and alkali metal carbonates such as sodium carbonate and potassium carbonate. Examples of the acids that can be used are hydrochloric acid, sulfuric acid, p-toluenesulfonic acid, phosphoric acid and trifluoromethanesulfonic acid.

The acid or alkali may be used in an amount of usually at least 2 equivalents, preferably 5 to 50 equivalents, per mole of the compound of formula (I-2-a).

The hydrolysis can be performed at a temperature of from about 0° C. to the refluxing temperature of the reaction mixture, but generally, temperatures of 50° C. to 120° C. are preferred.

Thus, the compound of formula (I-1-a) or its salt may be produced. This product can be separated from the reaction mixture, and/or purified, by customary methods such as filtration, centrifugal separation, extraction, recrystallization or chromatography.

The compound of formula (I-2-a) can be alkylated with a lower alkylating agent to form a compound of formula (I-1-b) through the compound of formula (I-2-b).

The lower alkylating agents that can be used for the alkylation may be any of those alkylating agents which can be usually employed for the alkylation of the active carbon atoms of aliphatic compounds. Suitable alkylating agents include lower alkyl halides such as methyl iodide, ethyl iodide and propyl iodide, and lower alkyl sulfates such as dimethyl sulfate or diethyl sulfate.

Prior to the alkylation with these lower alkylating agents, it is desirable to activate one hydrogen atom in accordance with the method shown in Reaction Scheme B, or protect it so that only one hydrogen atom of the two hydrogen atoms at the methylene moiety of the cyanomethyl group is easily and selectively alkylated.

Reaction Scheme B

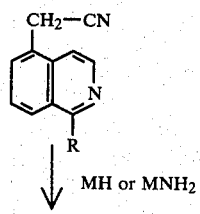
(I-2-a)

MH or MNH$_2$

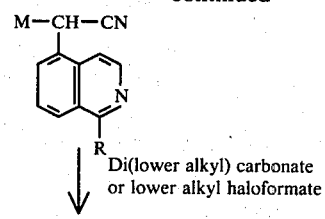
(I-2-a-1)

Di(lower alkyl) carbonate or lower alkyl haloformate

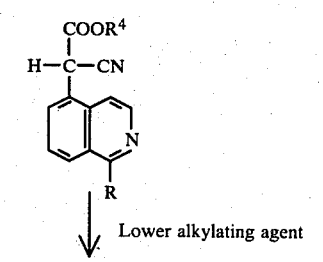
(I-2-a-2)

Lower alkylating agent

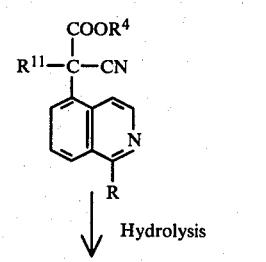
(I-2-a-3)

Hydrolysis

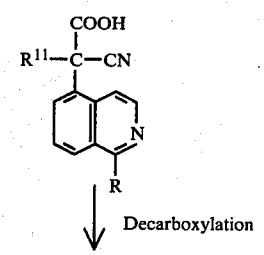
(I-2-a-4)

Decarboxylation

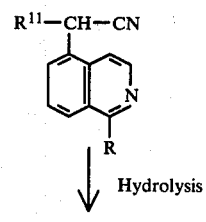
(I-2-b)

Hydrolysis

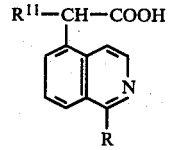
(I-1-b)

In the above formulae, $R^4$ represents a lower alkyl group, M represents an alkali metal (such as sodium, potassium or lithium), and $R^{11}$ and R are as defined above.

Treatment of the compound of formula (I-2-a) with an alkali metal hydride or an alkali metal amide (e.g., sodium hydride, potassium hydride, sodium amide, or potassium amide) and subsequent treatment with a di(-lower alkyl) carbonate or a lower alkyl haloformate (e.g., dimethyl carbonate, diethyl carbonate, methyl chloroformate, ethyl chloroformate, isopropyl chloroformate, or isobutyl chloroformate) may be carried out stepwise. However, these treatments can be carried out usually in one step by reacting the compound of formula (I-2-a) with the di(lower alkyl) carbonate or lower alkyl haloformate in the presence of the alkali metal hydride or alkali metal amide in a customary manner to convert it into the compound of formula (I-2-a-2).

The above reaction can be carried out in the absence or in the presence of a solvent. Suitable solvents which can be used may be ethers such as diethyl ether, tetrahydrofuran, dioxane, dimethoxyethane, and diethylene glycol dimethyl ether; sulfoxides such as dimethylsulfoxide; and aromatic hydrocarbons such as benzene or toluene. The reaction temperature is about 0° C. to the refluxing temperature of the reaction mixture, preferably 5° C. to 180° C. Or it is possible to allow the reactants to stand at room temperature for some time at the initial stage, and then react them while heating at a temperature of 50° C. to 150° C.

The resulting compound of formula (I-2-a-2) in which one of the hydrogen atoms of the methylene moiety of the cyanomethyl group is protected by an alkoxycarbonyl group (-COOR$^4$) is reacted with the lower alkylating agent described hereinabove.

This alkylation reaction can also be carried out either in the absence or presence of a solvent. The same solvents as exemplified above may be used. The temperature of the alkylation reaction is not critical, and can be varied over a wide range depending upon the type of the alkylating agent used. Generally, the temperature for alkylation is a temperature from room temperature to the refluxing temperature of the reaction mixture, especially a temperature of from 50° C. to 150° C.

The amount of the lower alkylating agent is neither critical. It can be varied depending upon the type of the lower alkylating agent and/or the reaction conditions, etc. Generally, the alkylating agent is used in an amount of at least 1.0 mole, preferably 3 to 10 moles, per mole of the compound of formula (I-2-a-2).

By hydrolyzing the resulting alkylated product of formula (I-2-a-3), for example, by heating it in the presence of an aqueous solution of an alkali such as sodium hydroxide or an inorganic acid such as hydrochloric acid or sulfuric acid in an organic solvent, the above compound may be converted easily to the compound (I-2-a-4). Then, the compound is heated usually in the absence of a solvent and in the absence or in the presence of an alkali, especially an alkali metal hydroxide such as sodium hydroxide or potassium hydroxide to decarboxylate it. Thus, the compound of formula (I-1-b), which corresponds to the compound of formula (I) in which R$^1$ represents a lower alkyl, can be obtained. The temperature for heating in this case is above the melting point of the compound of formula (I-2-a-4) but below the decomposition temperature of the compound of formula (I-2-b) when the decarboxylation is carried out in the absence of alkali. While in the presence of an alkali, the decarboxylation can be achieved by heating at a temperature lower than the melting point, for example to 50° C. to 120° C., the heating may of course be carried out at a temperature higher than the melting point.

The compound of formula (I-2-b) itself has anti-inflammatory and analgesic activities, and can be used as a medicine. By further hydrolyzing the above compound, it can be converted to the compound of formula (I-1-b) which has higher anti-inflammatory and analgesic activities. The hydrolysis of the compound of formula (I-2-b) can be carried out in the same way as in the hydrolysis of the compound of formula (I-2-a).

When the compound of formula (I-2-a-3) is hydrolyzed at the temperature described above with regard to the decarboxylation reaction, the final desired compound of formula (I-1-b) can be obtained directly.

In the series of reactions shown in Reaction Scheme B, the compound of formula (I-2-b) can also be prepared by reacting the compound of the following formula (I-2-a-1).

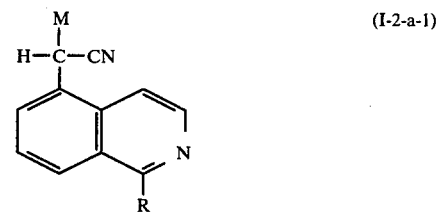

wherein R and M are as defined above, which is obtained advantageously by reacting the compound of formula (I-2-a) with an alkali metal hydride or alkali metal amide in an amount of not more than 1 equivalent, per mole of the compound of formula (I-2-a), with a lower alkylating agent mentioned above.

The alkylation of the compound of formula (I-2-a-1) can be performed by reacting the compound of formula (I-2-a-1) with a lower alkylating agent in the absence or in the presence of a solvent of the types exemplified above. The reaction temperature at this time is not critical, and can be varied widely depending upon the type of the alkylating agent. Generally, the reaction temperature is a temperature of from −10° C. to the refluxing temperature of the reaction mixture, preferably a temperature of from 0° C. to 80° C. The amount of the lower alkylating agent is neither critical, and can be varied over a wide range. Generally, it is advantageous to use the lower alkylating agent in an amount of at least 1 mole, especially 3 to 10 moles, per mole of the compound of formula (I-2-a-1).

The compound of formula (I-2-b) can be converted to the compound of formula (I-1-b) by hydrolysis in the same way as described above.

Alternatively, the compound of formula (I-1-a) may be subjected to the lower alkylating reaction shown by Reaction Scheme B to afford the compound of formula (I-1-b).

The resulting compound of formula (I-1-b) can be separated from the reaction mixture, and/or purified, in the manner described above.

The compound of formula (IX-1) obtained as an intermediate in the above Synthetic Route I may be converted to the desired compounds of formula (I-1-a) and (I-1-b) through the route shown in Reaction Scheme C below.

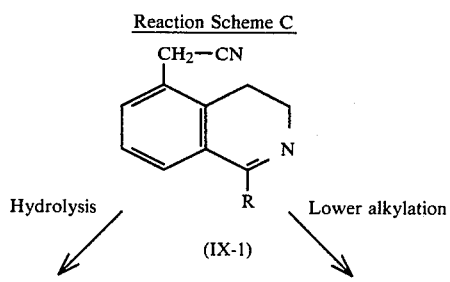

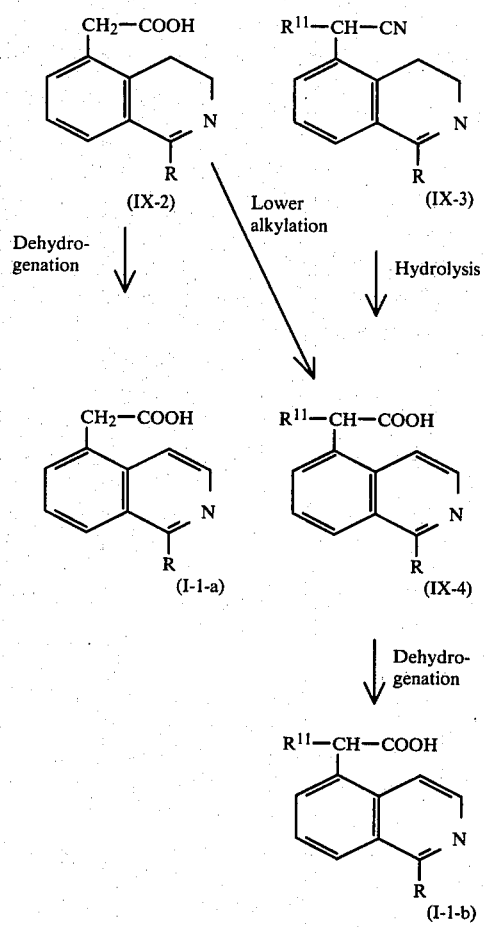

In the above formulae, $R^{11}$ and R are as defined above.

Hydrolysis of the compounds of formula (IX-1) and (IX-3); dehydrogenation of the compounds of formulae (IX-2) and (IX-4), and the lower alkylation of the compounds of formulae (IX-1) and (IX-2) can be performed by using the same conditions as described above.

The compounds of formulae (IX-1), (IX-2), (IX-3) and (IX-4), i.e. a group of compounds inclusively represented by the following formula

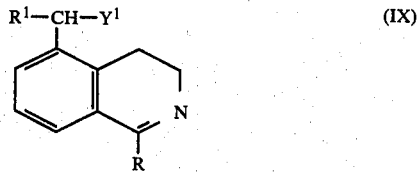
(IX)

wherein $R^1$, R and $Y^1$ are as defined above, are important intermediates for the production of the compound of formula (I). Furthermore, the compounds of formula (IX) are characterized by showing anti-inflammatory and analgesic activities, although they are lower than the activities of the compounds of formula (I).

Synthetic Route II

In Synthetic Route II in Reaction Scheme A, the reaction of the 1-amino-2-(2-chlorophenyl)ethane of formula (III) with the acyl halide of formula (IV), the dehydrocyclization of the resulting compound of formula (VII-A), and the subsequent dehydrogenation of the compound of formula (VII-B) can be carried out by using the same conditions as described above with regard to the amidation of the compound of formula (VI-A), the dehydrocyclization of the compound of formula (VI-D) and the subsequent dehydrogenation of the compound of formula (IX-1).

The compound of formula (VIII-C) so obtained can be converted to the compound of formula (VII-D) by cyanidation. This cyanidation can be carried out under similar conditions to those described above with regard to the cyanidation of the compound of formula (VI-C) in Synthetic Route I. This gives the compound of formula (VII-D).

Hydrolysis of the compound of formula (VII-D) gives the compound of formula (VII-E). This hydrolysis can be carried out by the same way as described above with regard to the hydrolysis of the compound of formula (I-2-a). This gives the compound of formula (VII-E).

Reduction of the resulting compound of formula (VII-E) or its ester affords the compound of formula (VII-F). This reduction can be carried out by contacting the compound of formula (VII-E) or its ester with a complex metal hydride such as lithium aluminum hydride or dihydro-bis(2-methoxyethoxy)aluminum sodium at a temperature from room temperature to the refluxing temperature of the reaction mixture usually in an inert solvent, for example, ethers such as ethyl ether, propyl ether, tetrahydrofuran, dioxane and dimethoxyethane, and aromatic hydrocarbons such as benzene, toluene or xylene.

Halogenation of the resulting compound of formula (VII-F) affords the compound of formula (X). This halogenation can be performed under the same conditions as described above on the halogenation of the compound of formula (VI-B) in Synthetic Route I.

Cyanidation of the compound of formula (X) affords the compound of formula (I-2-a) which is one of the desired compounds of this invention. This cyanidation can be carried out under the same conditions as described above on the cyanidation of the compound of formula (VI-C) in Synthetic Route I.

The compound of formula (I-2-a) obtained can be converted to the compound of formula (I-2-b), (I-1-a) or (I-1-b) of this invention as described in Synthetic Route I.

The compound of formula (VII-C) obtained in Synthetic Route II,

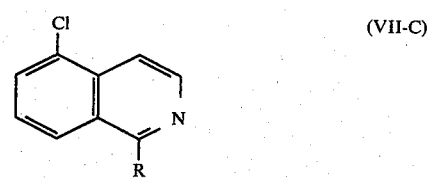
(VII-C)

wherein R is as defined above, can be directly converted to a compound of the following formula

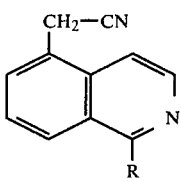

(I-2-a)

by reaction with acetonitrile (CH₃CN).

The above reaction can be carried out by contacting the compound of formula (VII-C) with acetonitrile in a suitable inert solvent such as liquid ammonia, methylamine, ethylamine, dimethylsulfoxide and dimethylformamide.

The reaction temperature is not critical, and can be varied over a wide range. Generally, it is desirable to carry out the reaction at $-40°$ C. to $200°$ C., preferably $-30°$ C. to room temperature. Advantageously, acetonitrile is used in an amount of usually at least 1 mole, preferably 1.5 to 5 moles, per mole of the compound of formula (VII-C).

The reaction with acetonitrile is advantageously carried out in the presence of at least one equivalent of a dehalogenating agent such as sodium amide, potassium amide, potassium butoxide, sodium methoxide or potassium ethoxide and a small amountt of a promoter such as iron trichloride.

The resulting compound of formula (I-2-a) can be converted to the compounds of formulae (I-2-b), (I-1-a) and (I-1-b) by a similar method to those mentioned above.

Synthetic Route III

According to Synthetic Route III of Reaction Scheme A, 1-cyano-2-benzoyl-1,2-dihydroisoquinoline of formula (V) is reacted with a compound of the formula $$R^{02}-X^4 \quad \text{(XI)}$$

wherein $X^4$ represents a halogen atom, especially a chlorine or bromine atom, and $R^{02}$ is as defined above, advantageously in the presence of an acid binder and a phase transfer catalyst, to form the compound of formula (VIII-A).

This reaction can be carried out in the absence of presence of a suitable inert organic solvent, for example aromatic hydrocarbons such as benzene or toluene, or ethers such as ethyl ether, tetrahydrofuran or dioxane. Advantageously, it is carried out in the absence of a solvent at room temperature. The ratio of the compounds of formula (V) to (XI) is not particularly limited. Advantageously, the compound of formula (XI) is used in an amount of generally 1 to 50 moles, preferably 1 to 5 moles, per mole of the compound of formula (V).

Suitable acid binders include alkali metal hydroxides such as sodium hydroxide or potassium hydroxide, and organic bases such as triethylamine, pyridine or dimethylaniline. The acid binder can be added in an amount of 1 to 10 equivalents, preferably 1 to 3 equivalents, per mole of the compound of formula (V). Examples of the phase transfer catalysts are benzyl triethyl ammonium chloride, tetraethyl ammonium bromide, tetrabutyl ammonium chloride, and tetrabutyl ammonium bromide. The phase transfer catalyst can be added in an amount of 0.005 to 0.1 mole, preferably 0.01 to 0.05 mole, per mole of the compound of formula (V).

The above reaction is desirably terminated within about 1 hour, preferably in amount 30 minutes. When the reaction is carried out for too long a time, it proceeds to an extent of forming the compound of formula (VIII-B), but its yield is extremely low.

The compound of formula (VIII-A) formed is then treated with a base to form the compound of formula (VIII-B). This treatment can be performed by contacting the compound of formula (VIII-A) with a base, for example organic bases such as Triton B, or alkali metal hydroxides such as sodium hydroxide or potassium hydroxide generally at room temperature in an inert solvent, for example, amides such as dimethylformamide, diethylformamide or dimethylacetamide; alcohols such as methanol, ethanol or benzyl alcohol; and ethers such as ethyl ether, tetrahydrofuran, dioxane and dimethoxyethane.

The amount of the base that can be used in this treatment is not critical. Generally, it is advantageous that the base is used in an amount of 1 to 20 equivalents, preferably 1 to 3 equivalents, per mole of the compound of formula (VIII-A). Desirably, the treatment of the compound of formula (VIII-A) is carried out under the above conditions for about 4 to 10 hours.

The compound of formula (VIII-B) thus obtained can then be changed to the compound of formula (VIII-C) by α-amidomethylation reaction. The α-amidomethylation reaction can be carried out by the so-called Tscherniac-Einhorn reaction which comprises reacting the compound of formula (VIII-B) with N-hydroxymethyl dichloroacetamide (Cl₂CHCONHCH₂OH) in the presence of conc. sulfuric acid or fuming sulfuric acid [see A. Einhorn et al., Ann. 348, 207 (1905), 361, 113 (1908)].

Thus, the compound of formula (VIII-C) can be obtained. Hydrolysis of this compound gives the compound of formula (VIII-D). This hydrolysis can be carried out in the same way as described above on the hydrolysis of the compound of formula (I-2-a-3).

Diazotization and hydrolysis of the resulting compound of formula (VIII-D) afford the compound of formula (VII-F).

Diazotization of the compound of formula (VIII-D) can be carried out by a method known per se, for example by treating the compound of formula (VIII-D) with sodium nitrite under ice cooling in an acidic aqueous medium. This affords the diazonium salt of the compound of formula (VIII-D). The diazonium salt is subjected to alkaline hydrolysis at an elevated temperature, preferably about 50° C. to about 80° C. For example, treatment with an aqueous solution of sodium hydroxide or potassium hydroxide can yield the compound of formula (VII-F).

The resulting compound of formula (VII-F) can be converted to the compounds of formulae (I-2-a), (I-2-b), (I-1-a) or (I-1-b) in the same manner as described above with regard to Synthetic Route II.

Synthetic Route IV

According to Synthetic Route IV in Reaction Scheme A, 1-amino-2-(2-methylphenyl)ethane of formula (XII) is reacted with the benzoyl halide derivative of formula (IV'). This reaction is usually carried out at a temperature of from room temperature to an elevated temperature, preferably about 15° C. to about 100° C., in an inert organic solvent, for example halogenated hydrocarbons such as dichloromethane, chloroform or carbon tetrachloride; aromatic hydrocarbons such as benzene, toluene or xylene; organic bases such as triethylamine, dimethylaniline or pyridine; or mixtures of these. The ratio of the compound of formulae (XII) to (IV') is not particularly limited. Generally, the compound of formula (IV') is added in an amount of 1 to 10 moles, preferably 1.1 to 2 moles, per mole of the compound of formula (XII).

The resulting compound of formula (XIII-A) is then dehydrocyclized. The dehydrocyclization can be carried out usually in the presence of a condensing agent at a temperature of at least about 50° C., preferably about 140° C. to about 250° C. Suitable condensing agents include, for example, phosphorus oxychloride, phosphorus oxybromide, sulfuric acid, phosphoric acid, phosphorus pentoxide, and polyphosphoric acid. Of these, phosphorus oxychloride and phosphorus pentoxide are advantageously used. The amount of the condensing agent is at least 1 equivalent, preferably 2 to 10 equivalents, per mole of the compound of formula (XIII-A).

The dehydrocyclization reaction can be carried out in the absence of a solvent. As required, it may be carried out in a suitable inert organic solvent such as benzene, toluene and xylene.

Dehydrogenation of the compound of formula (XIII-B) obtained by the dehydrocyclization affords the compound of formula (XIII-C). The dehydrogenation reaction can be carried out by treating the compound of formula (XIII-B) with a dehydrogenating agent in the absence of a solvent or in the presence of a suitable inert solvent, for example, hydrocarbons such as tetralin, benzene, toluene, xylene or mesitylene; water; acetic acid; and alcohols such as t-butanol and s-amyl alcohol. Suitable dehydrogenating agents include, for example, diphenyl disulfide, 2,3-dichloro-5,6-dicyanobenzoquinone, tetrachloro-1,4-benzoquinone, sulfur, selenium, chromic acid, and potassium permanganate. Of these, diphenyl disulfide is preferred. The amount of the dehydrogenating agent differs depending upon its type, etc. Generally, it can be used in an amount of at least 1 equivalent, preferably 1.1 to 10 equivalents, per mole of the compound of formula (XIII-B).

The reaction temperature is not critical, and can be varied over a wide range depending upon the type of the dehydrogenating agent, etc. Generally, temperatures of about 0° C. to about 300° C., preferably room temperature to about 210° C. may be used. Under the above conditions, the dehydrogenation reaction can be terminated generally in about 0.5 to 30 hours.

Thus, the compound of formula (XIII-C) is obtained. Halogenation of this compound gives the compound of formula (X). This halogenation is carried out by treating the compound of formula (XIII-C) with a halogenating agent in the absence of a solvent or in the presence of a suitable inert organic solvent, for example, halogenated hydrocarbons such as chloroform, carbon tetrachloride or perchloroethylene. Preferably, in order to promote the halogenation reaction, a small amount of a free radical generating reagent such as an organic peroxyacid such as benzoyl peroxide, is added and the reaction is performed under irradiation of light.

The reaction temperature of the halogenation is not particularly limited, and can be varied over a wide range. Desirably, the reaction is carried out generally at a temperature from room temperature to the refluxing temperature of the reaction mixture, preferably about 50° C. to the refluxing temperature of the reaction mixture.

Suitable halogenating agents include, for example, N-haloacid imides such as N-chlorosuccinimide and N-bromosuccinimide; molecular halogens such as chlorine or bromine, and N-haloacid amides such as N-bromoacetamide or N-chloroacetamide. Of these, N-bromosuccinimide is preferred. The amount of the halogenating agent is not strictly limited, and can be varied over a wide range depending upon the type of the halogenating agent used, etc. Generally, it is used in an amount of at least 1 equivalent, preferably 1 to 2 equivalents, per mole of the compound of formula (XIII-C).

The compound of formula (X) can be converted to the compound of formula (I-2-a), (I-2-b), (I-1-a) or (I-1-b) in the same way as described above on Synthetic Routes I and II.

Alternative route of synthesis of the compound of formula (I) in which $R^2$ represents a methylamino or dimethylamino group:

The compound of formula (I) in which $R^2$ represents a methylamino or dimethylamino group can be produced through Synthetic Route I, II or IV described above. It can alternatively be synthesized by preparing a compound of the following formula

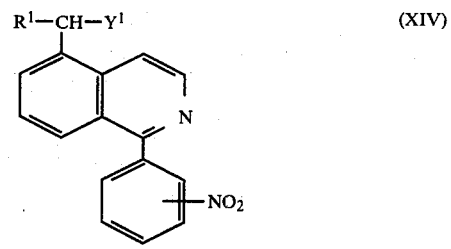

(XIV)

wherein $R^1$ and $Y^1$ are as defined above, from the corresponding starting material in the case of R or $R^{03}$ being a nitrophenyl group in accordance with Synthetic Route I, II or IV, reducing the compound of formula (XIV) to convert the nitro group into an amino group, and then methylating the amino group.

Reduction of the compound of formula (XIV) is carried out by catalytically hydrogenating the compound of formula (XIV), or treating it with nascent state hydrogen, or treating it with a complex metal hydride in a customary manner in a suitable inert solvent selected from water; ethers such as tetrahydrofuran, ethyl ether, dioxane or dimethoxyethane; aromatic hydrocarbons such as benzene, toluene or xylene; alcohols such as methanol and ethanol; organic acids such as acetic acid or propionic acid; mineral acids such as hydrochloric acid or sulfuric acid, and mixtures of these. When $Y^1$ in the compound of formula (XIV) is a carboxyl group, it is suitably protected prior to reduction.

Catalytic hydrogenation can be carried out in the presence of a hydrogenation catalyst such as palladium black, palladium-carbon, Raney nickel, Urushibara nicke, platinum, and rhodium under a hydrogen pressure ranging from atmospheric pressure to about 3 atmospheres at room temperature to about 50° C.

Treatment with nascent state hydrogen may be carried out usually at a temperature ranging from room temperature to the boiling point of the reaction mixture while generating nascent state hydrogen by contacting a metal such as iron, zinc, copper or tin with an organic acid such as acetic acid or an inorganic acid such as hydrochloric acid or sulfuric acid.

Suitable complex metal hydrides for use in the above reducing process include lithium aluminum hydride, sodium borohydride, and dihydro-bis(2-methoxyethoxy)aluminum sodium. The reduction is achieved by contacting the compound of formula (XIV) with the complex metal hydride at a temperature ranging from room temperature to the boiling point of the reaction mixture.

Thus, a compound of the formula

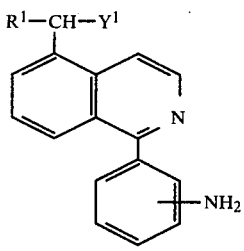

(XV)

wherein $R^1$ and $Y^1$ are as defined above, is obtained. This compound is subsequently methylated. The methylation canbbe performed in accordancw with methods usually employed in the methylation of amines. For example, the compound of formula (XV) is treated with a methylating agent such as dimethyl sulfate, or methyl halides (preferably $CH_3Br$), or formic acid/formalin. The suitable reaction temperature for the methylation is a temperature ranging from room temperature to the boiling point of the reaction mixture, preferably about 50° C. to about 100° C. The amount of the methylating agent is not critical, and may be 1 to 10 moles, preferably 1 to 5 moles, per mole of the compound of formula (XV) depending upon the degree of methylation (monomethylation or dimethylation). To perform monomethylation advantageously, it is desirable to protect one of the two hydrogen atoms of the amino group by, for example, a benzyl group.

Thus, a compound of the following formula

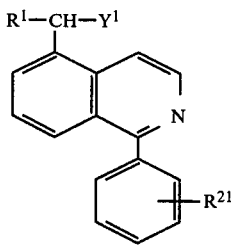

(XVI)

wherein $R^1$ and $Y^1$ are as defined above, and $R^{21}$ represents a methylamino or dimethylamino group, is obtained. A compound of formula (XVI) in which $Y^1$ is a cyano group can be converted to a compound of formula (XVI) in which $Y^1$ is a carboxyl group by hydrolysis in the manner described above.

The compound of formula (I)[i.e., formula (I-2-a), (I-2-b), (I-1-a), (I-1-b), or (XVI)] can be isolated and purified by conventional methods such as extraction, filtration, recrystallization or chromatography.

When the compound of formula (I) is in the form of a free acid or free base, it can be converted to its salt in a customary manner. Conversely, when it is in the form of a salt, it can be converted to a free acid or free base in a customary manner, too.

A compound of formula (I) in which Y is a carboxyl group can be converted to the corresponding compound of formula (I) in which Y is a lower alkoxycarbonyl group by reacting it in a customary manner with a lower alcohol or its reactive derivative. The compound of formula (I) in which Y is a lower alkoxycarbonyl group can also be obtained by alcoholysis of the corresponding compound of formula (I) in which Y is a cyano group in the presence of an acid catalyst using a lower alcohol.

The compound of formula (I) in which Y is a carboxyl group can be amidated with ammonia or a lower alkylamine in accordance with an ordinary peptide synthesizing method to form the corresponding compound of formula (I) in which Y is a carbamoyl group or a lower alkylaminocarbonyl group. The compound of formula (I) in which Y is a carbamoyl group can also be formed by hydrolyzing the corresponding compound of formula (I) in which Y is a cyano group, or aminating the corresponding compound of formula (I) in which Y represents a lower alkoxycarbonyl group.

The compounds of formula (I) of this invention described hereinabove generally have superior antiinflammatory and analgesic activities. Among them, compounds of the following formula

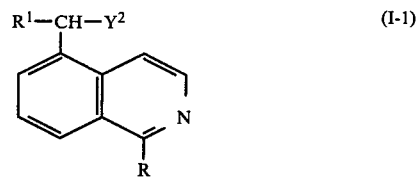

(I-1)

wherein R, $Y^2$ and $R^1$ are as defined above, and their salts, above all, compounds of formula (I-1) in which R represents an isopropyl group, a cyclopentyl group, a cyclohexyl group or a group of the formula

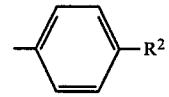

in which $R^2$ is as defined above, and $R^1$ represents a hydrogen atom, and their salts, have far higher anti-inflammatory and analgesic activities than phenylbutazone which is now accepted as a standard anti-inflammatory and analgesic agent in clinical medicine. Compounds of formula (I-1) in which $R^1$ is a hydrogen atom and R is a 4-chlorophenyl, 4-bromophenyl, 4-methylphenyl, 4-dimethylaminophenyl, isopropyl or cyclohexyl group, and their salts have higher anti-inflammatory and analgesic activities than indomethacin which is now known as the strongest anti-inflammatory and analgesic agent in clinical medicine. While anti-inflammatory and analgesic agents which have been known so far such as aspirin, phenylbutazone and indomethacin induce fairly heavy troubles in the digestive organs, the compounds of formula (I-1) of this invention have the marked therapeutic advantage that any troubles which may be caused to the digestive organs by these compounds are very slight.

The superior anti-inflammatory and analgesic activities of the compounds of this invention are substantiated by the following animal experiments.

The compounds of this invention used in the following animal experiments are shown by the following symbols.

Compounds

A: 1-(4-chlorophenyl)isoquinoline-5-acetic acid,
B: 1-(4-bromophenyl)isoquinoline-5-acetic acid,
C: 1-(4-fluorophenyl)isoquinoline-5-acetic acid,
D: 1-(4-dimethylaminophenyl)isoquinoline-5-acetic acid,
E: 1-(4-methylphenyl)isoquinoline-5-acetic acid,
F: 2-[1-(4-chlorophenyl)isoquinolin-5-yl]propionic acid,
G: 1-(4-methoxyphenyl)isoquinoline-5-acetic acid,
H: 1-phenylisoquinoline-5-acetic acid,
I: 1-(4-trifluoromethylphenyl)isoquinoline-5-acetic acid,
J: ethyl-1-phenylisoquinoline-5-acetate,
K: 1-phenylisoquinoline-5-acetamide,
L: 1-cyclohexylisoquinoline-5-acetic acid,
M: 1-isopropylisoquinoline-5-acetic acid,
N: 1-cyclopentylisoquinoline-5-acetic acid,
O: 1-isobutylisoquinoline-5-acetic acid,
P: 1-sec-butylisoquinoline-5-acetic acid.

(1) Anti-inflammatory activity

Male Wistar rats weighing 120 to 150 g which had been fasted for 24 hours were used in groups each consisting of 5 rats. In each group, the volumes of the left hind paw were measured by a volume differential meter (made by Ugo Basile Company), and each of the test compounds was suspended in an aqueous solution of 0.5% of carboxymethyl cellulose and 2.0% of Tween 80, and administered orally through a tube. After one hour from the administration, 0.1 ml of a 1% suspension of carrageenin in distilled water was subcutaneously injected into the plantar tissues of the left hind paw. Three hours later, the volumes of the left hind paw were again measured. The increase in volume of the left hind paw of each rat in each group (the volume of edema) was measured. The percent edema inhibition was calculated in accordance with the following equation, and the results are shown in Table 1.

TABLE 1

$$\text{Percent inhibition (\%)} = \frac{\left(\begin{array}{c}\text{Average increase}\\\text{in volume of left}\\\text{hind paw in the}\\\text{control group administered with}\\\text{the vehicle}\end{array}\right) - \left(\begin{array}{c}\text{Increase in volume}\\\text{of left hind paw}\\\text{in each rat in the}\\\text{groups administered}\\\text{with the test}\\\text{compound}\end{array}\right)}{\left(\begin{array}{c}\text{Average increase in}\\\text{volume of left hind}\\\text{paw in the control}\\\text{group administered}\\\text{with the vehicle}\end{array}\right)} \times 100$$

| Compound | Dosage (mg/kg, p.o.) | Percent inhibition (Average value ± Standard error) |
|---|---|---|
| A | 0.3 | 22.7 ± 6.1 |
|   | 1 | 27.3 ± 7.4 |
|   | 3 | 44.6 ± 5.8 |
| B | 0.3 | 26.8 ± 5.3 |
|   | 1 | 33.7 ± 6.1 |
|   | 3 | 48.2 ± 4.4 |
| C | 1 | 25.6 ± 3.4 |
|   | 3 | 28.3 ± 5.8 |
|   | 10 | 36.5 ± 4.0 |
| D | 1 | 16.3 ± 7.1 |
|   | 3 | 34.2 ± 5.6 |
| E | 10 | 42.1 ± 5.3 |
|   | 3 | 26.9 ± 5.2 |
|   | 10 | 49.5 ± 5.1 |
| F | 1 | 27.3 ± 6.3 |
|   | 3 | 33.1 ± 4.8 |
|   | 10 | 39.7 ± 5.1 |
| G | 1 | 13.1 ± 9.1 |
|   | 3 | 32.3 ± 6.3 |
|   | 10 | 41.2 ± 7.2 |
| H | 3 | 21.8 ± 4.5 |
|   | 10 | 31.0 ± 5.2 |
|   | 30 | 46.4 ± 7.7 |
| I | 3 | 17.0 ± 4.5 |
|   | 10 | 24.5 ± 7.1 |
|   | 30 | 30.2 ± 5.3 |
| J | 10 | 23.2 ± 6.1 |
|   | 30 | 41.1 ± 4.8 |
| K | 10 | 9.0 ± 6.4 |
|   | 30 | 39.7 ± 5.8 |
| L | 1 | 9.7 ± 2.0 |
|   | 3 | 17.4 ± 5.2 |
|   | 10 | 43.1 ± 4.3 |
| M | 1 | 19.3 ± 2.6 |
|   | 3 | 38.6 ± 3.2 |
|   | 10 | 62.9 ± 5.9 |
| N | 3 | 21.9 ± 8.1 |
|   | 10 | 24.8 ± 4.9 |
| O | 3 | 21.2 ± 7.8 |
|   | 10 | 30.3 ± 5.6 |
|   | 30 | 42.8 ± 8.8 |
| P | 3 | 15.9 ± 10.4 |
|   | 10 | 39.6 ± 7.0 |
| Indomethacin | 1 | 15.9 ± 6.2 |
|   | 3 | 29.8 ± 5.7 |
|   | 10 | 40.6 ± 5.1 |

(2) Analgesic activity

Male mice (ddY) weighing 18 to 22 g were used in groups each consisting of 10 mice. Each of the compounds was suspended in an aqueous solution of 0.5% of carboxymethyl cellulose and 2.0% of Tween 80, and administered orally through a tube. After one hour from the administration, 0.6% acetic acid was administered intraperitoneally in an amount of 0.1 ml per 10 g of body weight, and the number of writhings which occurred in the mice during a period of 20 minutes after the administration was measured. The percent inhibition was calculated from the following equation, and the $ED_{50}$ values of the test compounds were calculated from the percent inhibition in accordance with the method of Litchfield-Wilcoxon. The results are shown in Table 2.

TABLE 2

Percent inhibition (%) =

$$\frac{\left(\begin{array}{c}\text{Average number}\\ \text{of writhings in}\\ \text{the control group}\\ \text{administered with}\\ \text{the vehicle}\end{array}\right) - \left(\begin{array}{c}\text{Average number}\\ \text{of writhings in}\\ \text{the group ad-}\\ \text{ministered with}\\ \text{the test compound}\end{array}\right)}{\left(\begin{array}{c}\text{Average number of}\\ \text{writhings in the}\\ \text{control group ad-}\\ \text{ministered with}\\ \text{the vehicle}\end{array}\right)} \times 100$$

| Compound | $ED_{50}$ (mg/kg, p.o.) |
|---|---|
| A | 1.4 (0.7–2.5) |
| B | 1.0 (0.3–4.0) |
| C | 8.8 (4.0–19.4) |
| D | 0.11 (0.053–0.25) |
| E | 4.3 (1.4–12.9) |
| F | 3.2 (1.9–5.3) |
| G | 9.2 (3.4–24.8) |
| H | 4.1 (1.7–10.0) |
| L | 8.5 (2.8–25.5) |
| M | 3.5 (1.5–8.1) |
| Phenylbutazone | 109.0 (68.1–174.4) |
| Indomethacin | 0.21 (0.05–0.86) |

The numbers in the parentheses show 95% confidence limits.

(3) Ulcerogenic activity

Each of the test compounds was orally administered by the same way as in the test on anti-inflammatory activity to male Wistar rats weighing 120 to 150 g which had been fasted for 24 hours. Four hours later, they were killed with ether. Then, the stomach was removed from each rat, and the number of rats whose stomachs showed bleeding at the mucosal membrane and damage beneath the mucosal membrane was counted against the number of animals used. The results are shown in Table 3.

TABLE 3

| Compound | Dosage (mg/kg, p.o.) | Bleeding at the mucosal membrane | Damage beneath the mucosal membrane |
|---|---|---|---|
| A | 10 | 0/10 | 0/10 |
|   | 30 | 0/5 | 0/5 |
| B | 10 | 0/5 | 0/5 |
|   | 30 | 2/5 | 4/5 |
| D | 10 | 0/6 | 0/6 |
|   | 30 | 3/6 | 3/6 |
| E | 10 | 0/5 | 0/5 |
|   | 30 | 0/5 | 4/5 |
| F | 10 | 1/5 | 0/5 |
|   | 30 | 2/5 | 2/5 |
| G | 30 | 0/5 | 0/5 |
| H | 10 | 1/15 | 1/15 |
|   | 30 | 4/20 | 2/20 |
| L | 10 | 0/5 | 0/5 |
|   | 30 | 3/5 | 3/5 |
| Indomethacin | 3 | 1/6 | 1/6 |
|   | 10 | 5/6 | 5/6 |

In addition to the anti-inflammatory and analgesic activities, the compounds of formula (I) also have strong activity of inhibiting biosynthesis of prostaglandin and strong activity of inhibiting platelet aggregation.

(4) Activity of inhibiting prostaglandin synthesis

The activity of inhibiting prostaglandin synthesis was measured by adding a test compound, i.e. a substance having the activity of inhibiting prostaglandin synthesis, to a prostaglandin synthesizing reaction system shown below, and quantitatively determining to what extent synthesis of prostaglandin was inhibited.

Prostaglandin synthesizing reaction system 100 mM tris-HCl buffer (pH=8.0),
5 mM l-adrenalin,
5 mM glutathione,
50 μM arachidonic acid,
0.0125 μCi/ml (14c)-arachidonic acid,
1 mg/ml, as protein, of microsomes of bovine seminal vesicle (a prostaglandin synthesizing enzyme obtained by lyophylizing a microsome fraction prepared from bovine seminal vesicle).

The test compound was added to the reaction system to adjust the total amount to 1 ml. As a control, 1 ml of the above reaction system without addition of the test compound was provided. Each of these was incubated with shaking at 37° C. for 5 minutes, and 0.5 ml of 0.3 M citric acid was added to stop the reaction. The prostaglandin formed was extracted with ethyl acetate, fractionated by thin-layer chromatography. The radioactivity of each fraction was measured by a liquid scintillation counter. The amount of prostaglandin $E_2$ formed in the group to which the test compound had been applied was measured, and the percent inhibition was calculated in accordance with the following equation. From the percent inhibition, the $ED_{50}$ value of the test compounds was calculated in accordance with the Litchfield-Wilcoxon method. The $ED_{50}$ values of the test compounds are shown in Table 4 below.

Each of the test compounds was dissolved in distilled water as a sodium salt.

TABLE 4

Percent inhibition (%) =

$$\frac{\left(\begin{array}{c}\text{Amount of prosta-}\\ \text{glandin } E_2 \text{ formed}\\ \text{in the control}\\ \text{group}\end{array}\right) - \left(\begin{array}{c}\text{Amount of prosta-}\\ \text{glandin } E_2 \text{ formed}\\ \text{of the test com-}\\ \text{pound-applied group}\end{array}\right)}{\left(\begin{array}{c}\text{Amount of prostaglandin } E_2\\ \text{formed in the control group}\end{array}\right)} \times 100$$

| Test compound | $ED_{50}$ (μM) |
|---|---|
| A | 0.82 |
| Phenylbutazone | 26.1 |

(5) Activity of inhibiting platelet aggregation

Blood was drawn off from the abdominal artery of a male Hartley guinea pig under anesthesia with pentobarbital (40 mg/kg, i.p.) so that the mixing ratio of 3.8% citric acid solution and the whole blood became 1:9. The citrated blood was centrifuged at a speed of 1,000 rpm for 10 minutes. The supernatant was collected to obtain a platelet-rich plasma. Separately, it was centrifuged at a speed of 3,000 rpm for 15 minutes, and the supernatant was collected to obtain a platelet-poor plasma. The ability of platelet aggregation was measured by an SIENCO Dual Sample aggregometer (Model DP-247-E), adjusted in sensitivity to give light transmission values of 0 and 100%, respectively, for platelet-rich plasma and platelet-poor plasma. The platelet-rich plasma (250 μl) was placed in a cuvet, and preliminarily heated at 37° C. for 2 minutes, and then while stirring at a speed of 1,000 rpm, 31 μl of a test solution was added. The mixture was incubated for 2 minutes with stirring, and then 31 μl of a collagen solution was added, and the maximum aggregation rate of platelet was measured. The amount of the collagen applied was adjusted to the minimum effective amount which induced irreversible platelet aggregation. This amount was determined for each experiment. The percent inhibition of the test solution-applied group was determined in accordance with the following equation. From the percent inhibition, the $ED_{50}$ value of the test compounds was calculated in accordance with the Litchfield-Wilcoxon method. The $ED_{50}$ values of the test compounds are shown in Table 5. Each test compound was dissolved in distilled water as a sodium salt.

TABLE 5

Percent inhibition = (%)

$$\frac{\left(\begin{array}{l}\text{Maximum aggregation}\\\text{rate of platelet}\\\text{in the control}\\\text{group}\end{array}\right) - \left(\begin{array}{l}\text{Maximum aggregation}\\\text{rate of platelet in}\\\text{the test compound-}\\\text{applied group}\end{array}\right)}{\left(\begin{array}{l}\text{Maximum aggregation rate of}\\\text{platelet in the control group}\end{array}\right)} \times 100$$

| Compound | $ED_{50}$ (μM) |
|---|---|
| A | 1.9 (1.3–2.8) |
| Aspirin | 15.8 (10.4–24.0) |

The numbers in the parentheses show 95% confidence limits.

(6) Toxicity test

Each of the test compounds was suspended in a physiological saline solution having dissolved therein 2% of Tween 80, and orally administered through a tube to groups of ddY mice (male: 19 to 22 g) each group consisting of 6 mice. The mice were then observed for 1 week. The $LD_{50}$ values were calculated from the lethality in accordance with the method of Litchfield-Wilcoxon. The results are shown in Table 6.

TABLE 6

| Compound | $LD_{50}$ (mg/kg, p.o.) |
|---|---|
| A | 182 (142–233) |
| B | 182 (142–233) |
| C | >300 |
| D | >300 |
| E | >300 |
| G | >300 |
| H | >300 |
| L | >300 |
| M | 250 (117–535) |
| Indomethacin | 17.3 (9.9–30.1) |

The numbers in the parentheses show 95% confidence limits.

The compounds of this invention can therefore be used as active ingredients of drugs having anti-inflammatory and analgesic activities for the treatment and medication of man and other warm-blooded animals such as cattle, horses, swine, sheep, goats, rabbits and chickens so as to alleviate pains of various causes, reduce inflammation, inhibit thrombus formation, etc.

According to this invention, therefore, there is provided a pharmaceutical preparation having anti-inflammatory and analgestic activities, which comprises a therapeutically effective amount of the active compound of this invention having formula (I).

Any routes are available to administer the active compounds of this invention, for example oral administration, buccal administration and parenteral administration (e.g., intravenous injection, intramuscular injection, subcutaneous injection, intrarectal administration, topical administration). Oral administration is especially advantageous.

When the active compounds of this invention are used as medicines for man and animals, they are formulated into various dosage forms suitable for oral, buccal or parenteral administration according to methods known per se.

For example, the active compounds of this invention can be formulated into pharmaceutical preparations which together contain non-toxic pharmaceutically acceptable carriers or excipients normally used for pharmaceutical preparations of this kind. According to the intended uses, these pharmaceutical preparations can be made into a solid form (e.g., tablets, capsules, granules, powders, pellets, sugar-coated pills, trouches), a semi-solid form (e.g., ointments, creams, suppositories), and a liquid form (e.g., injectables, emulsions, suspensions, lotions, tinctures, sprays, syrups).

Examples of the non-toxic pharmaceutically acceptable carriers or excipients include starch, gelatin, glucose, lactose, fructose, maltose, magnesium carbonate, talc, magnesium stearate, methyl cellulose, carboxymethyl cellulose or its salts, gum arabic, polyalkylene glycols, distilled water for injection, alkyl p-hydroxybenzoates, syrup, ethanol, propylene glycol, glecerol, vaseline, and Carbowax.

These medicine may also contain therapeutically useful chemicals such as dispersants, antioxidants, preservatives, stabilizers, flavoring agents, binders, lusterants, salts for changing osmotic pressures, and buffers.

The amount of the active compound of this invention in the drug can be varied widely according, for example, to the dosage form of the drug. Generally, the amount is 0.1 to 100% by weight, preferably 0.5 to 95% by weight, based on the weight of the medicine. More specifically, it is desirable that the pharmaceutical preparation should contain the active compound of this invention in an amount of 1 to 100% by weight, preferably 10 to 95% by weight, when it is solid or semi-solid, and in an amount of 0.1 to 10%, preferably 0.5 to 5% by weight, when it is liquid.

The dosage of the active compound can be varied widely according to the type of the subject (whether it is man or another animal), the symptom, the physician's diagnosis, etc. Generally, it can be 0.05 to 30 mg/kg, preferably 0.1 to 20 mg/kg, per day. Higher or lower dosages can, of course, be used according to the symptom of a particular patinet, and the physician's diagnosis. The above dosage can be administered once or a plurality of times a day.

Compounds of formula (I) of this invention in which Y represents a cyano group, i.e. compounds of the following formula

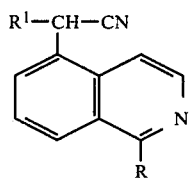

(I-2)

wherein R and $R^1$ are as defined above, are also important as intermediates for the synthesis of the compounds of formula (I-1) which have the superior pharmacological activities described above.

The following Examples illustrate the present invention in details.

EXAMPLE 1

Synthesis of 1-(4-Chlorophenyl)isoquinoline-5-acetonitrile:

(a) 1-Amino-2-(2-methylphenyl)ethane (13.5 g) was dissolved in 80 ml of pyridine. While the solution was cooled with stirring, 18 g of 4-chlorobenzoyl chloride was added dropwise. They were reacted at room temperature for 5 hours. Pouring of the reaction mixture into cold water gave a precipitate of crystals. The crystals were washed in water, dried, and recrystallized from cyclohexane to afford 19.2 g of 1-(4-chlorobenzoylamino)-2-(2-methylphenyl)ethane having a melting point of 95° to 96° C.

IR, $\nu_{KBr}{}^{cm-1}$: 3290, 1630.

NMR, $\delta_{CDCl_3}{}^{ppm}$: 2.35 (3H, singlet), 2.93 (2H, multiplet), 3.65 (2H, multiplet), 6.40 (1H, broad singlet), 7.12 (4H, singlet), 7.34 (2H, doublet), 7.60 (2H, doublet).

(b) Thirty-six (36) grams of 1-(4-chlorobenzoylamino)-2-(2-methylphenyl)ethane was dissolved in 180 ml of xylene and 100 ml of phosphorus oxychloride. While the solution was heated with stirring, 80 g of phosphorus pentoxide was added gradually, and the mixture was heated under reflux. The reaction mixture was poured into ice water. The aqueous layer was separated, and made weakly alkaline with ammonia water. Recrystallization of the precipitated oily product from n-hexane afforded 31 g of 1-(4-chlorophenyl)-5-methyl-3,4-dihydroisoquinoline as colorless prisms having a melting point of 66° to 67° C.

IR, $\nu_{KBr}{}^{cm-1}$: 2955, 1620, 1600, 1495, 1320, 1095, 840, 745.

NMR, $\delta_{CDCl_3}{}^{ppm}$: 2.35 (3H, singlet), 2.70 (2H, multiplet), 7.4 (7H, multiplet).

(c) A mixture of 30 g of 1-(4-chlorophenyl)-5-methyl-3,4-dihydroisoquinoline and 30 g of diphenyl disulfide was dissolved in 800 ml of tetralin, and the solution was heated. After the reaction, the tetralin was distilled off under reduced pressure. The residue was dissolved in benzene, and extracted with a 2 N aqueous solution of hydrochloric acid. The aqueous layer was neutralized with an aqueous solution of sodium hydroxide, extracted with ether, and dried, followed by distilling off the solvent. Recrystallization of the residue from benzenecyclohexane afforded 18 g of 1-(4-chlorophenyl)-5-methylisoquinoline as colorless needles having a melting point of 122° to 123.5° C.

IR, $\nu_{KBr}{}^{cm-1}$: 1606, 1495, 1410, 1095, 1020, 825, 760.

NMR, $\delta_{CDCl_3}{}^{ppm}$: 2.70 (3H, singlet), 7.5 (8H, multiplet), 8.60 (1H, doublet).

(d) 1-(4-Chlorophenyl)-5-methylisoquinoline (10.2 g) was dissolved in 50 ml of carbon tetrachloride. While the solution was heated under reflux and light was irradiated on it, 7.5 g of N-bromosuccinimide was added. The mixture was heated with stirring. After the reaction, the reaction mixture was cooled. The insoluble matter was removed by filtration. The filtrate was washed in water, dried, and concentrated to remove the solvent. Recrystallization from cold methanol afforded 9.2 g of 1-(4-chlorophenyl)-5-bromomethylisoquinoline as colorless needles having a decomposition point of 116° C.

IR, $\nu_{KBr}{}^{cm-1}$: 1600, 1485, 1100, 1015, 825, 815.

NMR, $\delta_{CDCl_3}{}^{ppm}$: 4.92 (2H, singlet), 7.5 (8H, multiplet), 8.70 (1H, doublet).

(e) To 2.6 g of sodium cyanide, 50 ml of dimethylsulfoxide and 3 ml of water was added 6.6 g of 1-(4-chlorophenyl)-5-bromomethylisoquinoline little by little. The mixture was stirred at room temperature for 2 hours, poured into water, and extracted with benzene. The extract was dried, and concentrated to afford 5.0 g of an oily product. The oily product was chromatographed, and recrystallized from dichloromethane-hexane to afford 4.1 g of 1-(4-chlorophenyl)isoquinoline-5-acetonitrile as slightly yellow prisms having a melting point of 131.5° to 132.5° C.

IR, $\nu_{KBr}{}^{cm-1}$: 2240, 1590, 1480, 1390, 1085, 1010, 820.

NMR, $\delta_{CDCl_3}{}^{ppm}$: 4.15 (2H, singlet), 7.55 (8H, multiplet), 8.70 (1H, doublet).

EXAMPLE 2

Synthesis of 1-(4-chlorophenyl)isoquinoline-5-acetonitrile:

(a) To 100 ml of carbon tetrachloride was added 14 g of 1-(4-chlorophenyl)-5-methylisoquinoline. While the solution was heated under reflux and light was irradiated on it, 7.5 g of N-chlorosuccinimide was added. The mixture was heated with stirring. After the reaction, the reaction mixture was cooled. The insoluble matter was removed by filtration. The filtrate was washed in water, and dried, followed by distilling off the solvent. Recrystallization of the residue from ether-hexane afforded 12.7 g of 1-(4-chlorophenyl)-5-chloromethylisoquinoline as light yellow prisms having a melting point of 101° to 102.5° C.

IR, $\nu_{KBr}{}^{cm-1}$: 1616, 1485, 1100, 1020, 825, 818.

NMR, $\delta_{CDCl_3}{}^{ppm}$: 5.04 (2H, singlet), 7.55 (8H, multiplet), 8.67 (1H, doublet).

(b) To a mixture of 5.0 g of sodium cyanide and 120 ml of dimethylsulfoxide was added 11.7 g of 1-(4-chlorophenyl)-5-chloromethylisoquinoline little by little. The mixture was stirred at room temperature for 2 hours, and poured into a mixture of ethyl acetate and 1% sodium bicarbonate aqueous solution. The organic layer was separated, washed with a saturated aqueous solution of sodium chloride, and dried. The solvent was distilled off. Recrystallization of the residue from dichloromethane-hexane afforded 1-(4-chlorophenyl)isoquinoline-5-acetonitrile as slightly yellow prisms having a melting point of 131.5° to 132.5° C.

EXAMPLE 3

Synthesis of 1-(4-chlorophenyl)isoquinoline-5-acetic acid:

2.0 g of 1-(4-chlorophenyl)isoquinoline-5-acetonitrile was heated under reflux together with 2.5 ml of conc. sulfuric acid, 5 ml of acetic acid and 2.5 ml of water.

After the reaction, the reaction mixture was poured into 10 ml of ice water, and neutralized with a 1 N aqueous solution of sodium hydroxide. The crystals precipitated were collected by filtration, and recrystallized from acetone to afford 1.9 g of 1-(4-chlorophenyl)-isoquinoline-5-acetic acid having a melting point of 233.5° to 236° C.

IR, $\nu_{KBr}^{cm-1}$: 2500, 1715, 1600, 1290, 1265, 1200, 1100, 1015, 840, 830, 755.

NMR, $\delta_{(CD_3)_2SO}^{ppm}$: 4.10 (2H, singlet), 7.6 (8H, multiplet), 8.60 (1H, doublet), 13.5 (1H, broad singlet).

EXAMPLE 4

Synthesis of 1-(4-bromophenyl)isoquinoline-5-acetonitrile:

(a) Forty (40) grams of 4-bromobenzoic acid was dissolved in 200 ml of dry dimethylformamide. While the solution was cooled with ice with stirring, 23 g of triethylamine and 22 g of ethyl chloroformate were added. After a lapse of 30 minutes, 28 g of 1-amino-2-(2-methylphenyl)ethane was added dropwise. The mixture was stirred at room temperature for 1 hour and then at 50° to 60° C. for 1 hour, and poured into ice water. The crystals precipitated were washed in water, dried, and recrystallized from cyclohexane to afford 49 g of 1-(4-bromobenzoylamino)-2-(2-methylphenyl)ethane as colorless needles having a melting point of 101.5° to 103.0° C.

IR, $\nu_{KBr}^{cm-1}$: 3320, 1640, 1590, 1540, 1480, 1310, 840, 740.

NMR, $\delta_{CDCl_3}^{ppm}$: 2.33 (3H, singlet), 2.92 (2H, multiplet), 3.64 (2H, multiplet), 6.3 (1H, broad singlet), 7.15 (4H, singlet), 7.52 (4H, singlet).

(b) Forty-four (44) grams of 1-(4-bromobenzoylamino)-2-(2-methylphenyl)ethane was heated with stirring at 140° C. for 4 hours together with 300 ml of xylene, 100 ml of phosphorus oxychloride and 100 g of phosphorus pentoxide. The reaction mixture was decanted to remove the solvent. The residue was carefully decomposed with ice water, and made weakly alkaline with an aqueous solution of sodium hydroxide. The crystals precipitated were extracted with benzene, and dried, followed by distilling off the solvent. Recrystallization of the residue from hexane afforded 35 g of 1-(4-bromophenyl)-5-methyl-3,4-dihydroisoquinoline as colorless needles having a melting point of 60.0° to 61.5° C.

IR, $\nu_{KBr}^{cm-1}$: 1613, 1310, 1170, 1010, 825, 742.

NMR, $\delta_{CDCl_3}^{ppm}$: 2.84 (3H, singlet), 2.72 (2H, multiplet), 3.80 (2H, multiplet), 7.13 (3H, multiplet), 7.48 (4H, singlet).

(c) Thirty-four (34) grams of 1-(4-bromophenyl)-5-methyl-3,4-dihydroisoquinoline was reacted for 8 hours together with 200 g of active manganese dioxide and 1000 ml of benzene. After the reaction, the manganese dioxide was removed by filtration, and the benzene was distilled off. Recrystallization of the resulting colorless crystals (29 g) from cyclohexane afforded 1-(4-bromophenyl)-5-methylisoquinoline as colorless needles having a melting point of 126.5° to 127.5° C.

IR, $\nu_{KBr}^{cm-1}$: 1590, 1482, 1393, 1080, 1010, 820, 775.

NMR, $\delta_{CDCl_3}^{ppm}$: 7.48 (4H, multiplet), 7.60 (4H, singlet), 8.60 (1H, doublet).

(d) 1-(4-Bromophenyl)-5-methylisoquinoline (26 g) was dissolved in 200 ml of carbon tetrachloride, and 17.6 g of N-bromosuccinimide was added. Under irradiation of light, the mixture was heated with stirring for 30 minutes. After the reaction, the insoluble matter was removed by filtration. The filtrate was washed in water, dried, and concentrated to remove the solvent. Thus, 1-(4-bromophenyl)-5-bromomethylisoquinoline was obtained. The product was dissolved in 150 ml of acetic acid, and 30 g of anhydrous sodium acetate was added. The mixture was stirred at 140° to 150° C. for 3 hours. After the reaction, the acetic acid was distilled off. The residue was poured into water, and neutralized with an aqueous solution of sodium hydroxide. The resulting oily product was extracted with benzene to afford 30 g of 1-(4-bromophenyl)-5-acetoxymethylisoquinoline. The product was heated with stirring for 2 hours together with 350 ml of methanol and 60 ml of 5 N sodium hydroxide. After the reaction, the reaction mixture was concentrated to remove the solvent. Water was added, and the crystals precipitated were collected by filtration. Recrystallization from benzene-tetrahydrofuran afforded 21 g of 1-(4-bromophenyl)-5-hydroxymethylisoquinoline having a melting point of 225.5° to 226.5° C.

IR, $\nu_{KBr}^{cm-1}$: 3190, 1595, 1400, 1100, 1015, 850, 830, 765.

NMR, $\delta_{(CD_3)_2SO}^{ppm}$: 5.00 (2H, singlet), 5.4 (1H, broad singlet), 7.65 (8H, multiplet), 8.56 (1H, doublet).

(e) 1-(4-Bromophenyl)-5-hydroxymethylisoquinoline (17 g) was dissolved in 300 ml of tetrahydrofuran, and 15 ml of phosphorus oxychloride was added. The mixture was stirred at room temperature for 1 hour. After the reaction, water was added, and the reaction mixture was neutralized with an aqueous solution of sodium hydroxide. The mixture was extracted with benzene, and dried. The solvent was distilled off. The residue was recrystallized from ether-hexane to afford 13.2 g of 1-(4-bromophenyl)-5-chloromethylisoquinoline as colorless prisms having a melting point of 115.5° to 118.5° C.

IR, $\nu_{KBr}^{cm-1}$: 1595, 1490, 1285, 1015, 825, 760.

NMR, $\delta_{CDCl_3}^{ppm}$: 5.02 (2H, singlet), 7.6 (8H, multiplet), 8.66 (1H, doublet).

(f) To a mixture of 2.5 g of sodium cyanide and 150 ml of dimethylsulfoxide was added 14 g of 1-(4-bromophenyl)-5-chloromethylisoquinoline little by little. The mixture was stirred at room temperature for 2 hours. The reaction mixture was poured into a mixture of ethyl acetate and a dilute aqueous solution of sodium bicarbonate. The organic layer was separated, dried, and recrystallized from dichloromethane-hexane to afford 8.5 g of 1-(4-bromophenyl)isoquinoline-5-acetonitrile as colorless prisms having a melting point of 121.5° to 122.5° C.

IR, $\nu_{KBr}^{cm-1}$: 2260, 1595, 1490, 1360, 1015, 828, 760.

NMR, $\delta_{CDCl_3}^{ppm}$: 4.16 (2H, singlet), 7,6 (7H, multiplet), 8.0 (1H, multiplet), 8.70 (1H, doublet).

EXAMPLE 5

Synthesis of 1-(4-bromophenyl)isoquinoline-5-acetic acid:

A mixture of 7.5 g of 1-(4-bromophenyl)isoquinoline-5-acetonitrile, 70 ml of acetic acid and 35 ml of 50% sulfuric acid was heated with stirring for 3 hours. After the reaction, water was added, and the pH of the reaction mixture was adjusted to 2 with an aqueous solution of sodium hydroxide. The crystals that precipitated were collected by filtration, and recrystallized from tetrahydrofuran-acetone to afford 7.0 g of 1-(4-bromophenyl)isoquinoline-5-acetic acid having a melting point of 230.5° to 232.5° C.

IR, $\nu_{KBr}^{cm-1}$: 2500, 1950, 1715, 1595, 1295, 1280, 1014, 754.

NMR, $\delta_{(CD_3)_2SO}^{ppm}$: 4.10 (2H, singlet), 7.65 (8H, multiplet), 8.56 (1H, doublet).

EXAMPLE 6

Synthesis of 1-(4-fluorophenyl)isoquinoline-5-acetonitrile:

(a) 1-Amino-2-(2-methylphenyl)ethane was reacted with 4-fluorobenzoyl chloride in the same way as in step (a) of Example 1 to afford 1-(4-fluorobenzoylamino)-2-(2-methylphenyl)ethane as colorless needles having a melting point of 82° to 83° C.

(b) 1-(4-Fluorobenzoylamino)-2-(2-methylphenyl)-ethane, phosphorus oxychloride and phosphorus pentoxide were reacted in the same way as in step (b) of Example 1 to afford 1-(4-fluorophenyl)-5-methyl-3,4-dihydroisoquinoline as colorless prisms having a melting point of 71.0 to 71.5° C.

(c) Diphenyl disulfide was reacted with 1-(4-fluorophenyl)-5-methyl-3,4-dihydroisoquinoline in the same way as in step (c) of Example 1 to afford 1-(4-fluorophenyl)-5-methylisoquinoline as colorless needles having a melting point of 91° to 92° C.

(d) 1-(4-Fluorophenyl)-5-methylisoquinoline was reacted with N-chlorosuccinimide in the same way as in step (a) of Example 2 to afford 1-(4-flurophenyl)-5-chloromethylisoquinoline as colorless needles having a melting point of 109.5° to 111.5° C.

(e) Sodium cyanide and 1-(4-fluorophenyl)-5-chloromethylisoquinoline were reacted in the same way as in step (b) in Example 2 to afford 1-(4-flurophenyl)isoquinoline-5-acetonitrile having a melting point of 136° to 136.5° C.

IR, $\nu_{KBr}^{cm-1}$: 2255, 1600, 1494, 1225, 1150.

NMR, $\delta_{CDCl_3}^{ppm}$: 4.17 (2H, singlet), 7.55 (8H, multiplet), 8.70 (1H, doublet).

EXAMPLE 7

Synthesis of 1-(4-fluorophenyl)isoquinoline-5-acetic acid:

1-(4-Fluorophenyl)isoquinoline-5-acetonitrile was treated in the same way as in Example 3 to afford 1-(4-fluorophenyl)isoquinoline-5-acetic acid as colorless needles having a melting point of 213.5° to 215.5° C.

IR, $\nu_{KBr}^{cm-1}$: 1705, 1604, 1515, 1222, 1155.

NMR, $\delta_{(CD_3)_2SO}^{ppm}$: 4.12 (2H, singlet), 7.6 (8H, multiplet), 8.60 (1H, doublet), 12.5 (1H, broad singlet).

EXAMPLE 8

Synthesis of 1-(4-methoxyphenyl)isoquinoline-5-acetonitrile:

(a) 1-Amino-2-(2-methylphenyl)ethane was reacted with 4-methoxybenzoyl chloride in the same way as in step (a) of Example 1 to afford 1-(4-methoxybenzoylamino)-2-(2-methylphenyl)ethane having a melting point of 81.8° to 82.1° C.

(b) 1-(4-Methoxybenzoylamino)-2-(2-methylphenyl)ethane, phosphorus oxychloride and phosphorus pentoxide were reacted in the same way as in step (b) of Example 1 to afford 1-(4-methoxyphenyl)-5-methyl-3,4-dihydroisoquinoline as colorless prisms having a melting point of 83.0° to 83.5° C.

(c) 1-(4-Methoxyphenyl)-5-methyl-3,4-dihydroisoquinoline and diphenyl disulfide were reacted in the same way as in step (c) of Example 1 to afford 1-(4-methoxyphenyl)-5-methylisoquinoline as colorless needles having a melting point of 60.4° to 60.8° C.

(d) 1-(4-Methoxyphenyl)-5-methylisoquinoline was reacted successively in the same way as in steps (d) and (e) of Example 1 to afford 1-(4-methoxyphenyl)isoquinoline-5-acetonitrile as slightly yellow scales having a melting point of 130.5° to 132.0° C.

IR, $\nu_{KBr}^{cm-1}$: 2250, 1619, 1260, 1182, 819.

NMR, $\delta_{CDCl_3}^{ppm}$: 3.88 (3H, singlet), 4.13 (2H, singlet), 7.50 (8H, multiplet), 8.66 (1H, doublet).

EXAMPLE 9

Synthesis of 1-(4-methoxyphenyl)isoquinoline-5-acetic acid:

1-(4-Methoxyphenyl)isoquinoline-5-acetonitrile was treated in the same way as in Example 3 to afford 1-(4-methoxyphenyl)isoquinoline-5-acetic acid as pale yellow crystals having a melting point of 210.3° to 211.2° C. (recrystallized from acetone).

IR, $\nu_{KBr}^{cm-1}$: 2420, 1930, 1710, 1612, 1260.

NMR, $\delta_{(CD_3)_2SO}^{ppm}$: 3.84 (3H, singlet), 4.08 (2H, singlet), 7.52 (8H, multiplet), 8.56 (1H, doublet).

EXAMPLE 10

Synthesis of 2-[1-(4-chlorophenyl)isoquinolin-5-yl]propionitrile:

(a) 1-(4-Chlorophenyl)isoquinoline-5-acetonitrile (2.6 g) was dissolved in 20 ml of diethyl carbonate, and 1.0 g of 50% oily sodium hydride was added. Then, 10 ml of dimethylsulfoxide was added, and 1.5 g of methyl iodide was added under cooling with water. The mixture was stirred for 1 hour. The reaction mixture was poured into water, extracted with ether, and dried. The solvent was distilled off. The resulting oily product was recrystallized from ether-hexane to afford ethyl 2-[1-(4-chlorophenyl)isoquinolin-5-yl]-2-cyanopropionate as colorless prisms having a melting point of 92° to 93.5° C.

IR, $\nu_{KBr}^{cm-1}$: 2250, 1750, 1590, 1255, 1240, 1100, 820.

NMR, $\delta_{COCl_3}^{ppm}$: 1.25 (3H, triplet), 2.25 (3H, singlet), 4.30 (2H, quartet), 7.5 (8H, multiplet), 8.65 (1H, doublet).

(b) Ethyl 2-[1-(4-chlorophenyl)isoquinolin-5-yl]-2-cyanopropionate (1.0 g) was heated under reflux together with 40 ml of ethanol, 0.20 g of sodium hydroxide and 2 ml of water. After the reaction, the reaction mixture was concentrated under reduced pressure. The resulting oily product was extracted with ether, and dried. The solvent was distilled off, and the residue was recrystallized from ether-hexane to afford 0.5 g of 2-[1-(4-chlorophenyl)isoquinolin-5-yl]propionitrile as colorless needles having a melting point of 127.5° to 130° C.

IR, $\nu_{KBr}^{cm-1}$: 2250, 1590, 1560, 1490, 1095, 1015, 830.

NMR, $\delta_{CDCl_3}^{ppm}$: 1.84 (3H, doublet), 4.60 (1H, quartet), 7.5 (8H. multiplet), 8.66 (1H, doublet).

EXAMPLE 11

Synthesis of 2-[1-(4-chlorophenyl)isoquinolin-5-yl]propionic acid:

Ethyl-2-[1-(4-chlorophenyl)isoquinolin-5-yl]-2-cyanopropionate (1.0 g) was heated over an oil bath at 150° C. together with 2 ml of conc. sulfuric acid, 4 ml of acetic acid and 2 ml of water. After the reaction, the reaction mixture was poured into water. The pH of the mixture was adjusted to 4 with a 1 N aqueous solution of sodium hydroxide. The crystals that precipitated were extracted with dichloromethane, and dried over anhydrous sodium sulfate. The solvent was distilled off, and the residue was recrystallized from dichloromethane-hexane to afford 2-[1-(4-chlorophenyl)isoquinolin-5-yl]propionic acid as colorless prisms having a melting point of 199.5° to 202.0° C.

IR, $\nu_{KBr}cm^{-1}$: 2600–2400, 1720, 1600, 1490, 1220, 1100, 825.

NMR, $\delta_{CDCl_3}ppm$: 1.70 (3H, doublet), 4.45 (1H, quartet), 7.5 (8H, multiplet), 8.61 (1H, doublet), 11.2 (1H, singlet).

EXAMPLE 12

Synthesis of 1-(4-dimethylaminophenyl)isoquinoline-5-acetic acid:

(a) One hundred and fifty (150) grams of methyl 2-cyanomethylbenzoate ("Yakugaku Zasshi", Vol. 86, p. 544, 1966) was added dropwise to a suspension of 60 g of lithium aluminum hydride and 211 g of aluminium chloride in ether while maintaining the suspension at −20° C. The mixture was stirred at room temperature for 5 hours, and the aluminum complex was decomposed with 520 ml of a 10 N aqueous solution of sodium hydroxide and 140 ml of water. The residue was extracted with tetrahydrofuran, dried, and distilled under reduced pressure to afford 45 g of 1-amino-2-(2-hydroxymethylphenyl)ethane as a colorless oil having a boiling point of 125° C./0.5 mmHg.

IR, $\nu_{KBr}cm^{-1}$: 3400–3000, 2880, 2960, 1600, 1460, 1030, 760.

NMR, $\delta_{CDCl_3}ppm$: 2.87 (4H, multiplet), 2.98 (3H, singlet), 4.55 (2H, singlet), 7.1–7.4 (4H, multiplet).

(b) 1-Amino-2-(2-hydroxymethylphenyl)ethane (10.2 g) was dissolved in 40 ml of pyridine, and with stirring under ice cooling, 25 g of 4-nitrobenzoyl chloride was added gradually. The mixture was stirred at room temperature for 4 hours and then at 50° C. for 1 hour, and poured into ice water. The crystals precipitated were washed in water, dried, and recrystallized from tetrahydrofuran-benzene to afford 24.3 g of 1-(4-nitrobenzoyl)-amino-2-[2-(4-nitrobenzoyloxymethyl)phenyl]ethane having a melting point of 168.2° to 169.7° C.

IR, $\nu_{KBr}cm^{-1}$: 3310, 1730, 1645, 1535, 1515, 1355, 1285, 1100, 720.

NMR, $\delta_{(CD_3)_2SO}ppm$: 2.8–3.8 (5H, multiplet), 5.49 (2H, singlet), 7.2–9.05 (12H, multiplet).

(c) 1-(4-Nitrobenzoyl)amino-2-[2-(4-nitrobenzoyloxymethyl)phenyl]ethane (24 g) was added to a solution of 300 ml of methanol, 2.6 g of sodium hydroxide and 100 ml of water. The mixture was refluxed for 1 hour. After the reaction, the solvent was distilled off, and water was added. The crystals that precipitated were collected by filtration, washed with water, and recrystallized from ethanol-n-hexane to afford 14.8 g of 1-(4-nitrobenzoyl)amino-2-(2-hydroxymethylphenyl)ethane having a melting point of 137.3° to 137.6° C.

IR, $\nu_{KBr}cm^{-1}$: 3280, 1639, 1598, 1560, 1515, 1330, 1000.

NMR, $\delta_{CDCl_3}ppm$: 2.8–3.3 (4H, multiplet), 3.55–3.95 (2H, multiplet), 4.8 (2H, doublet), 7.28 (4H, singlet), 7.81 (2H, doublet), 8.17 (2H, doublet).

(d) 1-(4-Nitrobenzoyl)amino-2-(2-hydroxymethylphenyl)ethane (15.3 g) was dissolved in 200 ml of chloroform, and with stirring under ice cooling, 15.9 g of phosphorus pentachloride was added gradually. The mixture was stirred at room temperature for 8 hours, and then the solvent was distilled off. The residue was dissolved in benzene, washed in water, and dried, followed by distilling off the solvent. The residue was recrystallized from benzene-n-hexane to afford 15.7 g of 1-(4-nitrobenzoyl)amino-2-(2-chloromethylphenyl)ethane having a melting point of 125.9° to 126.3° C.

IR, $\nu_{KBr}cm^{-1}$: 3320, 1635, 1600, 1555, 1518, 1359, 1300, 842.

NMR, $\delta_{CDCl_3}ppm$: 3.09 (2H, triplet), 3.8 (2H, quartet), 4.18 (2H, singlet), 6.1–6.6 (1H, broad singlet), 7.2–7.45 (4H, multiplet), 7.32 (2H, doublet), 8.24 (2H, doublet).

(e) Sodium cyanide (2.9 g) was dissolved in 100 ml of dimethylsulfoxide, and with stirring at room temperature, 15.5 g of 1-(4-nitrobenzoyl)amino-2-(2-chloromethylphenyl)ethane was gradually added. The reaction was performed at room temperature for 10 hours. The reaction mixture was poured into water, extracted with ethyl acetate, washed in water, and dried. The solvent was distilled off, and the residue was recrystallized from ethanol to afford 11.2 g of 1-(4-nitrobenzoyl)amino-2-(2-cyanomethylphenyl)ethane having a melting point of 118.6° to 119.1° C.

IR, $\nu_{KBr}cm^{-1}$: 3400, 2250, 1660, 1602, 1535, 1520, 1355, 863, 762, 708.

NMR, $\delta_{CDCl_3}ppm$: 2.8–3.2 (2H, multiplet), 3.5–3.95 (4H, multiplet), 6.3–6.8 (1H, broad singlet), 7.15–7.5 (4H, multiplet), 7.85 (2H, doublet), 8.24 (2H, doublet).

(f) 1-(4-Nitrobenzoyl)amino-2-(2-cyanomethylphenyl)-ethane (12.7 g) was dissolved in 128 ml of xylene and 77 ml of phosphorus oxychloride. While the solution was heated with stirring over an oil bath at 140° C., 38 g of phosphorus pentoxide was added gradually. The reaction was performed for 7 hours. The upper layer of the reaction mixture was removed by decantation. Ice water was added to the residue, and an aqueous solution of sodium hydroxide was added to make it neutral. The crystals that precipitated were collected by filtration, and recrystallized from ethanol to afford 9 g of 1-(4-nitrophenyl)-3,4-dihydroisoquinoline-5-acetonitrile having a melting point of 137.7° to 138.7° C.

IR, $\nu_{KBr}cm^{-1}$: 2240, 1615, 1600, 1519, 1350.

NMR, $\delta_{CDCl_3}ppm$: 2.65–2.98 (2H, multiplet), 3.72–4.12 (4H, multiplet), 7.0–7.6 (4H, multiplet), 7.72 (2H, doublet), 8.27 (2H, doublet).

(g) Six (6) grams of 1-(4-nitrophenyl)-3,4-dihydroisoquinoline-5-acetonitrile and 5 g of diphenyl disulfide were reacted for 6 hours over an oil bath at 165° C. After the reaction, the reaction mixture was extracted with chloroform, chromatographed, and recrystallized from acetone-n-hexane to afford 2.5 g of 1-(4-nitrophenyl)-isoquinoline-5-acetonitrile having a melting point of 218.9° to 219.3° C.

IR, $\nu_{KBr}cm^{-1}$: 2260, 1605, 1520, 1355.

NMR, $\delta_{CDCl_3}ppm$: 4.19 (2H, singlet), 7.25–8.85 (9H, multiplet).

(h) 1-(4-Nitrophenyl)isoquinoline-5-acetonitrile (2.1 g) was dissolved in 12 ml of 75% sulfuric acid and 2 ml of acetic acid, and refluxed for 3 hours. The reaction mixture was poured into ice water, and washed with ether. The aqueous layer was neutralized with an aqueous solution of sodium hydroxide. The crystals that precipitated were collected by filtration, and recrystallized from tetrahydrofuran to afford 2.1 g of 1-(4-nitrophenyl)isoquinoline-5-acetic acid having a melting point of 252.2° to 253.8° C.

IR, $\nu_{KBr}cm^{-1}$: 1722, 1598, 1515, 1350, 1280.

NMR, $\delta_{(CD_3)_2SO}ppm$: 3.0–3.7 (1H, broad singlet), 4.12 (2H, singlet), 7.4–8.7 (9H, multiplet).

(i) 1-(4-Nitrophenyl)isoquinoline-5-acetic acid (5.0 g) was dissolved in 300 ml of ethanol, and 4.0 ml of conc. sulfuric acid was added. The mixture was heated for 6 hours. After the reaction, the solvent was distilled off. Benzene was added to the residue. It was washed in water and dried. The solvent was distilled off, and the residue was recrystallized from ethane-hexane to afford 4.8 g of ethyl 1-(4-nitrophenyl)isoquinoline-5-acetate as colorless needles having a melting point of 89.5° to 90.5° C.

IR, $\nu_{KBr}^{cm-1}$: 1730, 1520, 1352, 1315, 1210, 1180.

NMR, $\delta_{CDCl_3}^{ppm}$: 1.25 (3H, triplet), 4.09 (2H, singlet), 4.20 (2H, quartet), 7.80 (6H, multiplet), 8.36 (2H, doublet), 8.66 (1H, doublet).

(j) Ethyl 1-(4-nitrophenyl)isoquinoline-5-acetate (4.2 g) was dissolved in 100 ml of ethanol, and 1.0 g of 10% palladium-carbon was added. The reaction was carried out in a stream of hydrogen. After the reaction, the catalyst was removed by filtration, and the filtrate was concentrated under reduced pressure. The residue was recrystallized from ether to afford 3.4 g of ethyl 1-(4-aminophenyl)isoquinoline-5-acetate having a melting point of 129.0° to 132.5° C.

IR, $\nu_{KBr}^{cm-1}$: 3470, 3365, 1728, 1625, 1190.

NMR, $\delta_{CDCl_3}^{ppm}$: 1.24 (3H, triplet), 2.9 (2H, broad singlet), 4.05 (2H, singlet), 4.16 (2H, quartet), 6.78 (2H, doublet), 7.5 (5H, multiplet), 8.13 (1H, multiplet), 8.60 (1H, doublet).

(k) Ethyl 1-(4-aminophenyl)isoquinoline-5-acetate (2.0 g) was dissolved in 10 ml of 90% formic acid, and 1.1 g of 37% formalin was added. The reaction was performed at 100° C. for 1 hour. The reaction mixture was concentrated under reduced pressure, and the residue was dissolved in ethyl acetate and washed with a dilute aqueous solution of sodium bicarbonate. The organic layer was dried, and the solvent was distilled off. The resulting oily product was chromatographed. From a 3% ethanolic chloroform eluate, 1.2 g of ethyl 1-(4-dimethylaminophenyl)isoquinoline-5-acetate was obtained.

Melting point: 132.0° to 135.0° C. (recrystallized from ether-hexane)

IR, $\nu_{KBr}^{cm-1}$: 1730, 1612, 1410, 1360, 1350, 1190, 810.

NMR, $\delta_{CDCl_3}^{ppm}$: 1.24 (3H, triplet), 3.04 (6H, singlet), 4.05 (2H, singlet), 4.18 (2H, quartet), 6.86 (2H, doublet), 7.6 (5H, multiplet), 8.20 (;H, multiplet), 8.60 (1H, doublet).

(l) Ethyl 1-(4-dimethylaminophenyl)isoquinoline-5-acetate (0.5 g) was heated for 1.5 hours with 40 ml of ethanol and 4 ml of a 5 N aqueous solution of sodium hydroxide. The reaction mixture was concentrated under reduced pressure. Water was added to the residue, and it was treated with activated carbon. Acetic acid was added to acidify the treated residue. Yellow crystals which precipitated were collected by filtration, dried, and then recrystallized from tetrahydrofuran-acetone to afford 0.35 g of 1-(4-dimethylaminophenyl)isoquinoline-5-acetic acid.

Melting point: 209° to 212° C.

IR, $\nu_{KBr}^{cm-1}$: 2920, 2480, 1920, 1710, 1610, 1525, 1355, 815.

NMR, $\delta_{(CD_3)_2SO}^{ppm}$: 3.00 (6H, singlet), 4.08 (2H, singlet), 6.85 (2H, doublet), 7.6 (5H, multiplet), 8.05 (1H, multiplet), 8.52 (1H, doublet).

EXAMPLE 13

Synthesis of 1-(4-methylphenyl)isoquinoline-5-acetonitrile:

(a) 1-Amino-2-(2-chlorophenyl)ethane (44.5 g) was dissolved in 140 ml of pyridine, and with stirring under cooling, 44.5 g of p-toluoyl chloride was added dropwise. The reaction was performed at room temperature for 3 hours. The reaction mixture was poured into ice water, and the crystals that precipitated were collected by filtration. The crystals were dissolved in benzene, washed successively with hydrochloric acid, water and saturated aqueous sodium chloride solution, and dried. The solvent was distilled off. The residue was recrystallized from benzene to afford 72 g of 1-(p-toluoylamino)-2-(2-chlorophenyl)ethane as colorless needles having a melting point of 106.0° to 108.5° C.

IR, $\nu_{KBr}^{cm-1}$: 3360, 2970, 1630, 1546, 1330, 760.

NMR, $\delta_{CDCl_3}^{ppm}$: 2.38 (3H, singlet), 3.05 (2H, triplet), 3.66 (2H, multiplet), 6.50 (1H, broad singlet), 7.19 (5H, multiplet), 7.61 (2H, doublet).

(b) 1-(p-Toluoylamino)-2-(2-chlorophenyl)ethane (70 g) was dissolved in 700 ml of xylene and 320 ml of phosphorus oxychloride, and while the solution was heated with stirring, 240 g of phosphorus pentoxide was added. The mixture was heated under reflux for 4 hours. Water was added to the reaction mixture. The aqueous layer was made weakly alkaline with an aqueous solution of sodium hydroxide, extracted with benzene, washed in water, and dried. The solvent was distilled off, and the residue was recrystallized from benzene to afford 29 g of 1-(4-methylphenyl)-5-chloro-3,4-dihydroisoquinoline as colorless needles.

Melting point: 82.7° to 83.4° C.

IR, $\nu_{KBr}^{cm-1}$: 1612, 1445, 824, 740.

NMR, $\delta_{CDCl_3}^{ppm}$: 2.41 (3H, singlet), 2.90 (2H, multiplet), 3.83 (2H, multiplet), 7.30 (7H, multiplet).

(c) 1-(4-Methylphenyl)-5-chloro-3,4-dihydroisoquinoline (29 g) and 24.7 g of diphenyl disulfide were reacted over an oil bath at 220° C. The reaction mixture was dissolved in cyclohexane, and extracted with a 4 N aqueous solution of hydrochloric acid. The aqueous layer was neutralized with an aqueous solution of sodium hydroxide. The resulting oily product was extracted with benzene, washed in water, and dried. The solvent was distilled off, and the residue was recrystallized from benzene to afford 22.5 g of 1-(4-methylphenyl)-5-chloroisoquinoline as colorless needles having a melting point of 88.6° to 89.1° C.

IR, $\nu_{KBr}^{cm-1}$: 1619, 1346, 1131, 820, 755.

NMR, $\delta_{CDCl_3}^{ppm}$: 2.48 (3H, singlet), 7.49 (8H, multiplet), 8.70 (1H, doublet).

(d) A mixture of 22 g of 1-(4-methylphenyl)-5-chloroisoquinoline, 74.4 g of copper cyanide and 420 ml of hexamethylphosphotriamide was heated overnight under reflux. After the reaction, the reaction mixture was poured into a mixture of ethylenediamine, water and benzene, and stirred for 30 minutes. The mixture was then filtered through Celite. The benzene layer as filtrate was washed in water, and dried, followed by distilling off the solvent. The residue was recrystallized from ether to afford 16.4 g of 1-(4-methylphenyl)-5-cyanoisoquinoline as colorless needles having a melting point of 131.8° to 132.4° C.

IR, $\nu_{KBr}^{cm-1}$: 2210, 1602, 1549, 1343, 818, 760.

NMR, $\delta_{CDCl_3}^{ppm}$: 2.49 (3H, singlet), 7.49 (8H, multiplet), 8.76 (1H, doublet).

(e) 1-(4-Methylphenyl)-5-cyanoisoquinoline (16.4 g) was dissolved in 50 ml of conc. sulfuric acid and 50 ml of water, and the solution was heated under reflux for 3 hours. The reaction mixture was poured into water, and the crystals that precipitated were collected by filtration, dried, and dissolved in 200 ml of ethanol. Conc. sulfuric acid (30 ml) was added, and the mixture was heated under reflux for 4 hours. The reaction mixture was poured into water, and neutralized with potassium carbonate. The resulting oily product that precipitated was extracted with benzene, washed in water, and dried. The solvent was distilled off, and the residue was recrystallized from ether to afford 14.5 g of 1-(4-methylphenyl)-5-ethoxycarbonylisoquinoline as slightly yellow prisms having a melting point of 112.1° to 112.3° C.

IR, $\nu_{KBr}^{cm-1}$: 2998, 1710, 1250, 1130, 830, 760.

NMR, $\delta_{CDCl_3}^{ppm}$: 1.48 (3H, triplet), 2.47 (3H, singlet), 4.48 (2H, quartet), 7.42 (5H, multiplet), 8.34 (2H, multiplet), 8.72 (2H, singlet).

(f) 1-(4-Methylphenyl)-5-ethoxycarbonylisoquinoline (14.5 g) was dissolved in 200 ml of anhydrous tetrahydrofuran, and with stirring under cooling, lithium aluminum hydride (suspended in 100 ml of tetrahydrofuran) was added dropwise. The mixture was stirred at room temperature for 1 hour. Water and a 20% aqueous solution of sodium hydroxide were added to the reaction mixture, and the mixture was stirred for 30 minutes. The reaction mixture was filtered through Celite. The filtrate was concentrated, and the residue was recrystallized from benzene to afford 7.5 g of 1-(4-methylphenyl)-5-hydroxymethylisoquinoline as colorless needles.

Melting point: 195.0°–195.2° C.

IR, $\nu_{KBr}^{cm-1}$: 3160, 1394, 1092, 825.

NMR, $\delta_{CDCl_3}^{ppm}$: 2.46 (3H, singlet), 2.60 (1H, broad singlet), 5.12 (2H, singlet), 7.48 (8H, multiplet), 8.58 (1H, doublet).

(g) 1-(4-Methylphenyl)-5-hydroxymethylisoquinoline (7.5 g) was dissolved in 80 ml of chloroform, and 12.5 g of phosphorus pentachloride was added under ice cooling. The mixture was stirred at room temperature for 1 hour, and 100 ml of water was added. The mixture was stirred for 30 minutes, and neutralized with potassium carbonate. The chloroform layer was washed in water, and dried. The solvent was distilled off, and the residue was recrystallized from methanol to afford 8.6 g of 1-(4-methylphenyl)-5-chloromethylisoquinoline as slightly yellow prisms having a melting point of 119.8° to 120.1° C.

IR, $\nu_{KBr}^{cm-1}$: 1616, 1592, 1382, 826, 770, 672.

NMR, $\delta_{CDCl_3}^{ppm}$: 2.47 (3H, singlet), 5.04 (2H, singlet), 7.50 (8H, multiplet), 8.69 (2H, doublet).

(h) Sodium cyanide (1.89 g) was dissolved in 100 ml of dimethylsulfoxide, and 8.6 g of 1-(4-methylphenyl)-5-chloromethylisoquinoline was added. At room temperature, the mixture was stirred for 1 hour. After the reaction, the reaction mixture was poured into water, extracted with ether, washed in water, and dried. The solvent was distilled off. The residue was recrystallized from ether to afford 7 g of 1-(4-methylphenyl)isoquinoline-5-acetonitrile as prisms having a melting point of 101.7° to 102.1° C.

IR, $\nu_{KBr}^{cm-1}$: 2224, 1616, 1592, 817.

NMR, $\delta_{CDCl_3}^{ppm}$: 2.48 (3H, singlet), 4.13 (2H, singlet), 7.49 (8H, multiplet), 8.68 (1H, doublet).

EXAMPLE 14

Synthesis of 1-(4-methylphenyl)isoquinoline-5-acetic acid:

1-(4-Methylphenyl)isoquinoline-5-acetonitrile (7 g) was treated in the same way as in Example 3 to afford 5.7 g of 1-(4-methylphenyl)isoquinoline-5-acetic acid as colorless prisms having a melting point of 222.9° to 223.7° C.

IR, $\nu_{KBr}^{cm-1}$: 3440, 2480, 1930, 1719, 1270, 824, 760.

NMR, $\delta_{(CD_3)_2SO}^{ppm}$: 2.44 (3H, singlet), 4.10 (2H, singlet), 7.56 (8H, multiplet), 8.68 (1H, doublet).

EXAMPLE 15

Synthesis of 1-phenylisoquinoline-5-acetonitrile:

(a) 1-Amino-2-(2-chlorophenyl)ethane and benzoyl chloride were reacted in the same way as in step (a) of Example 13 to afford 1-benzoylamino-2-(2-chlorophenyl)-ethane having a melting point of 70.1° to 71.0° C. (b) 1-Benzoylamino-2-(2-chlorophenyl)ethane, phosphorus oxychloride and phosphorus pentoxide were reacted in the same way as in step (b) of Example 13 to afford 1-phenyl-5-chloro-3,4-dihydroquinoline as an oil. (c) 1-Phenyl-5-chloro-3,4-dihydroisoquinoline and diphenyl disulfide were reacted in the same way as in step (c) of Example 13 to afford 1-phenyl-5-chloroisoquinoline as colorless needles having a melting point of 66.0° to 66.6° C. (d) 1-Phenyl-5-chloroisoquinoline, copper cyanide and hexamethylphosphotriamide were reacted in the same way as in step (d) of Example 13 to afford 1-phenyl-5-cyanoisoquinoline as an oil. (e) 1-Phenyl-5-cyanoisoquinoline was treated in the same way as in step (e) of Example 13 to afford 1-phenyl-5-methoxycarbonylisoquinoline as colorless needles having a melting point of 102.2° to 103.1° C. (f) 1-Phenyl-5-methoxycarbonylisoquinoline and dihydrobis(2-methoxyethoxy)aluminum sodium (in 70% benzene) were reacted in the same way as in step (f) of Example 13 to afford 1-phenyl-5-hydroxymethylisoquinoline as colorless plates having a melting point of 97.3° to 97.9° C. (g) 1-Phenyl-5-hydroxymethylisoquinoline was treated in the same way as in step (g) of Example 13 to afford 1-phenyl-5-chloromethylisoquinoline having a melting point of 104.0° to 104.2° C. (h) 1-Phenyl-5-chloromethylisoquinoline was treated by the same way as in step (h) of Example 13 to afford 1-phenylisoquinoline-5-acetonitrile as an oil.

IR, $\nu_{KBr}^{cm-1}$: 2250, 1620, 1595, 1560, 1495, 1415, 1390, 1360, 815, 760, 700.

NMR, $\delta_{CDCl_3}^{ppm}$: 4.16 (2H, singlet), 7.22–8.22 (9H, multiplet), 8.73 (1H, doublet).

EXAMPLE 16

Synthesis of 1-phenylisoquinoline-5-acetonitrile:

Metallic sodium (1.15 g) was added to 100 ml of liquid ammonia, and 1.3 g of acetonitrile and 2.39 g of 1-phenyl-5-chloroisoquinoline were added to the solution. A small amount of iron trichloride was added, and the reaction was performed for 5 hours. After the reaction, ammonia was distilled off, and ice water was carefully added to the residue. The resulting oily product was extracted with ether, and dried over anhydrous sodium sulfate. The solvent was distilled off, and the residue was chromatographed to afford 1-phenylisoquinoline-5-acetonitrile as an oil.

EXAMPLE 17

Synthesis of 1-phenylisoquinoline-5-acetic acid:

1-Phenylisoquinoline-5-acetonitrile was treated in the same was as in Example 3 to afford 1-phenylisoquinoline-5-acetic acid as needles having a melting point of 191.7° to 192.4° C.

IR, $\nu_{KBr}^{cm-1}$: 1710, 1615, 1600, 1295, 1265.

NMR, $\delta_{(CD_3)_3SO}^{ppm}$: 4.11 (2H, singlet), 7.4–8.1 (9H, multiplet), 8.6 (1H, doublet).

EXAMPLE 18

Synthesis of 1-isopropylisoquinoline-5-acetonitrole:

(a-1-1) A mixture of 26 g of 1-cyano-2-benzoyl-1,2-dihydroisoquinoline [Org. Synth. Coll. vol. 4, 641 (1963)] and 1 g of benzyl triethyl ammonium chloride was dissolved in 50 ml of isopropyl bromide. Then, 80 g of a 50% aqueous solution of sodium hydroxide was added, and the mixture was stirred at room temperature for 30 minutes. The product was extracted with benzene. The solvent was distilled off, and the residue was recrystallized from ethanol to afford 20 g of 1-cyano-1-isopropyl-2-benzoyl-1,2-dihydroisoquinoline as colorless scales having a melting point of 123.8° to 126.0° C.

IR, $\nu_{KBr}^{cm-1}$: 2220, 1680, 1634, 1338, 1322, 1255, 780, 702.

NMR, $\delta_{CDCl_3}^{ppm}$: 0.87 (3H, doublet), 1.16 (3H, doublet), 2.92 (1H, multiplet), 5.75 (1H, doublet), 6.50 (1H, doublet), 7.46 (9H, multiplet), (a-1-2) 1-Cyano-1-siopropyl-2-benzoyl-1,2-dihydroisoquinoline (19 g) was dissolved in 120 ml of dry dimethylformamide in a stream of nitrogen, and 24 ml of a 30% methanol solution of Triton B was added. The mixture was stirred at room temperature for 6 hours. The reaction mixture was poured into water, extracted with benzene, and dried. The solvent was distilled off. Distillation under reduced pressure gave 10.2 g of 1-isopropylisoquinoline.

Boiling point: 99° to 101° C./0.5 mmHg

IR, $\nu_{neat}^{cm-1}$: 1621, 1582, 1384, 1009, 820, 748.

NMR, $\delta_{CDCl_3}^{ppm}$: 1.46 (6H, doublet), 3.92 (1H, multiplet), 7.45 (5H, multiplet), 8.45 (1H, doublet).

(a-2-1) A mixture of 20 g of 1-cyano-2-benzoyl-1,2-dihydroisoquinoline and 1 g of benzyl trimethyl ammonium chloride was dissolved in 100 ml of acetone. The solution was stirred for 10 minutes, and 60 ml of a 50% aqueous solution of sodium hydroxide was added. The mixture was stirred for 3 hours at room temperature. The product was extracted with benzene, washed in water, and dried, followed by distilling off the solvent. The residue was recrystallized from cyclohexane to afford 25 g of 1-(1-benzoyloxy-1-methylethyl)isoquinoline having a melting point of 116.2° to 118.8° C.

IR, $\nu_{KBr}^{cm-1}$: 2960, 1720, 1286, 1107, 820, 710.

NMR, $\delta_{CDCl_3}^{ppm}$: 2.13 (6H, singlet), 7.46 (10H, multiplet), 8.47 (1H, multiplet).

(a-2-2) Ten grams of 1-(1-benzoyloxy-1-methylethyl)-isoquinoline was dissolved in 100 ml of ethanol, and 2 g of 10% palladium-carbon was dissolved. The mixture was stirred in a stream of hydrogen at room temperature and atmospheric pressure for 24 hours. The reaction mixture was filtered through Celite, and the solvent was distilled off. Distillation under reduced pressure afforded 4.0 g of 1-isopropylisoquinoline. (b) A mixture of 9.4 g of 1-isopropylisoquinoline and 12 g of N-hydroxymethyl dichloroacetamide was dissolved in 94 g of conc. sulfuric acid and 9.5 g of 20% fuming sulfuric acid, and the solution was heated for 3 hours. The reaction mixture was poured into water, made weakly alkaline with an aqueous solution of sodium hydroxide, and extracted with ethyl acetate. The solvent was distilled off, and the residue was recrystallized from ethyl acetate-benzene to afford 20 g of 1-isopropyl-5-dichloroacetylaminomethylisoquinoline having a melting point of 150.7° to 151.0° C.

IR, $\nu_{KBr}^{cm-1}$: 3250, 1670, 1556, 1207, 810.

NMR, $\delta_{CDCl_3}^{ppm}$: 1.44 (6H, doublet), 3.90 (1H, multiplet), 3.89 (2H, doublet), 5.97 (1H, singlet), 6.93 (1H, broad singlet), 7.56 (3H, multiplet), 8.24 (1H, multiplet), 8.53 (1H, doublet).

(c) Twenty grams of 1-isopropyl-5-dichloroacetylaminomethylisoquinoline was dissolved in 100 ml of conc. hydrochloric acid. The solution was heated with stirring for 1 hour. The reaction mixture was concentrated, made weakly alkaline with an aqueous solution of sodium hydroxide, and extracted with benzene to afford 8.7 g of 1-isopropyl-5-aminomethylisoquinoline as an oil.

IR, $\nu_{neat}^{cm-1}$: 3360, 3320, 3050, 1612, 1592, 1564, 810, 750.

NMR, $\delta_{CDCl_3}^{ppm}$: 1.42 (6H, doublet), 1.65 (2H, singlet), 3.95 (1H, multiplet), 4.27 (2H, singlet), 7.59 (3H, multiplet), 8.14 (1H, multiplet), 8.52 (1H, doublet).

(d) 1-iso-Propyl-5-aminomethylisoquinoline (8.7 g) was dissolved in 20 ml of acetic acid and 20 ml of water, and with ice cooling, 9 g of sodium nitrite was added. The mixture was stirred for 30 minutes. Then, 30 ml of a 10 N aqueous solution of sodium hydroxide was added, and the mixture was heated for 1 hour. The product was extracted with ethyl acetate, washed in water, and dried, followed by distilling off the solvent. Recrystallization of the residue from methylene chloride/n-hexane afforded 7.1 g of 1-isopropyl-5-hydroxymethylisoquinoline as colorless needles having a melting point of 119.9° to 120.9° C.

IR, $\nu_{KBr}^{cm-1}$: 3300, 1612, 1592, 1564, 810, 750.

NMR, $\delta_{CDCl_3}^{ppm}$: 1.44 (6H, doublet), 2.66 (1H, broad singlet), 3.92 (1H, multiplet), 5.11 (2H, singlet), 7.63 (3H, multiplet), 8.17 (1H, multiplet), 8.48 (1H, doublet).

(e) 1-iso-Propyl-5-hydroxymethylisoquinoline (6.5 g) was dissolved in 50 ml of chloroform and 6.5 ml of phosphorus oxychloride was added dropwise under ice cooling. The mixture was stirred at room temperature for 1 hour. Water (50 ml) was added to the reaction mixture, and it was made weakly alkaline with potassium carbonate. The chloroform layer was washed in water, and dried. The solvent was distilled off under reduced pressure to afford 7.1 g of 1-isopropyl-5-chloromethylisoquinoline as a colorless oil.

IR, $\nu_{neat}^{cm-1}$: 2960, 1616, 1592, 1565, 1270, 1096, 810, 750.

NMR, $\delta_{CDCl_3}^{ppm}$: 1.44 (6H, doublet), 3.93 (1H, multiplet), 4.97 (2H, singlet), 7.62 (3H, multiplet), 8.24 (1H, multiplet), 8.48 (1H, doublet).

(f) 1-iso-Propyl-5-chloromethylisoquinoline (7 g) was added to 70 ml of a dimethylsulfoxide solution of 1.87 g of sodium cyanide, and the mixture was stirred for 30 minutes. The reaction mixture was poured into water, and extracted with ethyl acetate, washed in water, and dried. The solvent was distilled off, and the residue was recrystallized from ether-n-hexane to afford 5.5 g of 1-siopropylisoquinoline-5-acetonitrile as colorless needles having a melting point of 61.8° to 62.2° C.

IR, $\nu_{KBr}^{cm-1}$: 2965, 2220, 1617, 1592, 1565, 1093, 810, 750.

NMR, $\delta_{CDCl_3}^{ppm}$: 1.42 (6H, doublet), 3.96 (1H, multiplet), 4.09 (2H, singlet), 7.60 (3H, multiplet), 8.27 (1H, multiplet), 8.69 (1H, doublet).

EXAMPLE 19

Synthesis of 1-isopropylisoquinoline-5-acetonitrile:

(a) Isoquinoline and N-hydroxymethyl dichloroacetamide were reacted in the same way as in step (b) of Example 18 to afford 5-dichloroacetylaminomethylisoquinoline having a melting point of 162.0° to 162.4° C. (b) 5-Dichloroacetylaminomethylisoquinone was hydrolyzed in the same way as in step (c) of Example 18 to afford 5-aminomethylisoquinoline as an oil. (c) 5-Aminoethylisoquinoline was diazotized and hydrolyzed in the same way as in step (d) of Example 18 to afford 5-hydroxymethylisoquinoline havng a melting point of 79.5° to 80.7° C. (d) 5-Hydroxymethylisoquinoline was halogenated in the same way as in step (e) of Example 18 to afford 5-chloromethylisoquinoline. (e) 5-Chloromethylisoquinoline was treated in the same way as in step (f) of Example 18 to afford 5-cyanomethylisoquinoline having a melting point of 130.4° to 131.2° C.

IR, $\delta_{KBr}^{cm-1}$: 2960, 2223, 1620, 1595, 816, 770.

NMR, $\nu_{CDCl_3}^{ppm}$: 4.12 (2H, singlet), 7.80 (4H, multiplet), 8.65 (1H, doublet), 9.31 (1H, singlet).

(f) 5-Cyanomethylisoquinoline (4.9 g), 5.7 g of potassium cyanide and 200 mg of benzyl triethyl ammonium chloride were dissolved in 60 ml of dichloromethane and 12 ml of water. The solution was stirred for 30 minutes, and 8.2 g of benzoyl chloride was added dropwise. The mixture was further stirred for 4 hours. After the reaction, the dichloromethane layer was washed in water, and dried, followed by distilling off the solvent. The residue was recrystallized from ether to afford 4.5 g of 1-cyano-2-benzoyl-5-cyanomethyl-1,2-dihydroisoquinoline as colorless prisms having a melting point of 66.4° to 69.7° C.

IR, $\nu_{KBr}^{cm-1}$: 2220, 1668, 1629, 1348, 1275, 776.

NMR, $\delta_{CDCl_3}^{ppm}$: 3.80 (2H, singlet), 6.08 (1H, doublet), 6.55 (1H, singlet), 6.79 (1H, doublet), 7.45 (8H, multiplet).

(g) 1-Cyano-2-benzoyl-5-cyanomethyl-1,2-dihydroisoquinoline, benzyl triethyl ammonium chloride and acetone were reacted in the same way as in step (a-2-1) of Example 18 to afford 1-(1-benzoyloxy-1-methylethyl)-5-cyanomethylisoquinoline as a colorless oil.

IR, $\delta_{neat}^{cm-1}$: 3000, 2222, 1720, 1300, 1105, 760, 715.

NMR, $\nu_{CDCl_3}^{ppm}$: 2.14 (6H, singlet), 4.06 (2H, singlet), 7.52 (9H, multiplet), 8.62 (2H, multiplet).

(h) 1-(1-Benzoyloxy-1-methylethyl)-5-cyanomethylisoquinoline was reduced in the same way as in step (a-2-2) of Example 18 to afford 1-isopropylisoquinoline-5-acetonitrile.

EXAMPLE 20

Synthesis of 1-isopropylisoquinoline-5-acetic acid:

1-iso-Propylisoquinoline-5-acetonitrile was treated in the same way as in Example 3 to afford 1-isopropylisoquinoline-5-acetic acid as slightly yellow prisms having a melting point of 180.7° to 181.9° C.

IR, $\nu_{KBr}^{cm-1}$: 3440, 2990, 2420, 1960, 1710, 1605, 1210, 820, 764.

NMR, $\delta_{(CD_3)_2SO}^{ppm}$: 1.34 (6H, doublet), 4.00 (1H, multiplet), 4.05 (2H, singlet), 7.67 (3H, multiplet), 8.22 (1H, multiplet), 8.46 (1H, doublet).

EXAMPLE 21

Synthesis of 1-cyclohexylisoquinoline-5-acetonitrile:

(a) 1-Amino-2-(2-chlorophenyl)ethane and cyclohexanecarbonyl chloride was reacted in the same way as in step (a) of Example 13 to afford 1-cyclohexylcarbonylamino-2-(2-chlorophenyl)ethane having a melting point of 93.5° to 93.9° C.

IR, $\nu_{KBr}^{cm-1}$: 3260, 2930, 1640, 1550, 742.

NMR, $\delta_{CDCl_3}^{ppm}$: 0.9–2.3 (11H, multiplet), 2.96 (2H, multiplet), 3.46 (2H, multiplet), 5.4–5.9 (1H, broad singlet), 7.0–7.5 (4H, multiplet).

(b) 1-Cyclohexylcarbonylamino-2-(2-chlorophenyl)-ethane, phosphorus oxychloride and phosphorus pentoxide were reacted in the same was as in step (b) of Example 13 to afford 1-cyclohexyl-5-chloro-3,4-dihydroisoquinoline as an oil.

IR, $\nu_{KBr}^{cm-1}$: 2940, 2860, 1630, 1445.

NMR, $\delta_{CDCl_3}^{ppm}$: 1.05–2.1 (10H, multiplet), 2.5–3.1 (3H, multiplet), 3.5–3.8 (2H, multiplet), 7.0–7.55 (3H, multiplet).

(c) 1-Cyclohexyl-5-chloro-3,4-dihydroisoquinoline and diphenyl disulfide were reacted in the same way as in step (c) of Example 13 to afford 1-cyclohexyl-5-chloroisoquinoline as an oil.

IR, $\nu_{KBr}^{cm-1}$: 2940, 2870, 1610, 1580, 1350, 815, 755.

NMR, $\delta_{CDCl_3}^{ppm}$: 1.1–2.2 (10H, multiplet), 3.25–3.8 (1H, multiplet), 7.2–8.25 (4H, multiplet), 8.56 (1H, doublet).

(d) 1-Cyclohexyl-5-chloroisoquinoline, copper cyanide and hexamethylphosphotriamide were reacted in the same way as in step (d) of Example 13 to afford 1-cyclohexyl-5-cyanoisoquinoline having a melting point of 94.7° C.

IR, $\nu_{KBr}^{cm-1}$: 2940, 2850, 2230, 1610, 1593, 1563, 820, 763.

NMR, $\delta_{CDCl_3}^{ppm}$: 1.1–2.2 (10H, multiplet), 3.3–3.8 (1H, multiplet), 7.25–8.75 (5H, multiplet).

(e) 1-Cyclohexyl-5-cyanoisoquinoline was treated in the same way as in step (e) of Example 13 to afford 1-cyclohexyl-5-ethoxycarbonylisoquinoline as an oil.

IR, $\nu_{KBr}^{cm-1}$: 2940, 2860, 1720, 1265, 1245, 1205, 1105.

NMR, $\delta_{CDCl_3}^{ppm}$: 1.2–2.2 (13H, multiplet), 3.2–3.8 (1H, multiplet), 4.45 (2H, quartet), 7.21–8.6 (5H, multiplet).

(f) 1-Cyclohexyl-5-ethoxycarbonylisoquinoline and lithium aluminum hydride were reacted in the same way as in Example 13, step (f) to afford 1-cyclohexyl-5-hydroxymethylisoquinoline as an oil.

IR, $\nu_{KBr}^{cm-1}$: 3300, 2930, 2860, 1570, 1450, 810.

NMR, $\delta_{CDCl_3}^{ppm}$: 0.8–2.2 (10H, multiplet), 2.4–2.9 (1H, broad singlet), 3.15–3.9 (1H, multiplet), 5.09 (2H, singlet), 7.2–8.26 (4H, multiplet), 8.46 (1H, doublet).

(g) 1-Cyclohexyl-5-hydroxymethylisoquinoline and phosphorus oxychloride were reacted in the same way as in step (g) of Example 13 to afford 1-cyclohexyl-5-chloromethylisoquinoline having a melting point of 88.4° to 89.4° C.

IR, $\nu_{KBr}^{cm-1}$: 2940, 2870, 1570, 821.

NMR, $\delta_{CDCl_3}^{ppm}$: 1.1–2.15 (10H, multiplet), 3.2–3.8 (1H, multiplet), 4.96 (2H, singlet), 7.23–8.35 (4H, multiplet), 8.56 (1H, doublet).

(h) 1-Cyclohexyl-5-chloromethylisoquinoline and sodium cyanide were reacted in the same way as in step (h) of Example 13 to afford 1-cyclohexylisoquinoline-5-acetonitrile having a melting point of 85.3° to 85.6° C.

IR, $\nu_{KBr}^{cm-1}$: 2940, 2860, 2260, 1560, 1565, 1415, 1350, 815.

NMR, $\delta_{CDCl_3}^{ppm}$: 1.2–2.2 (10H, multiplet), 3.26–3.82 (1H, multiplet), 4.08 (2H, singlet), 7.3–8.4 (4H, multiplet), 8.56 (1H, doublet).

EXAMPLE 22

Synthesis of 1-cyclohexylisoquinoline-5-acetic acid:

1-Cyclohexylisoquinoline-5-acetonitrile was treated in the same way as in Example 3 to afford 1-cyclohexylisoquinoline-5-acetic acid as colorless crystals having a melting point of 178.5° to 179.1° C.

IR, $\nu_{KBr}{}^{cm-1}$: 2940, 2865, 2700–2280, 1725, 1265, 1170, 815.

NMR, $\delta_{(CD_3)_2SO}{}^{ppm}$: 1.2–2.1 (10H, multiplet), 3.1–3.8 (1H, multiplet), 4.02 (2H, singlet), 7.5–8.35 (4H, multiplet), 8.42 (1H, doublet).

EXAMPLE 23

Synthesis of 1-cyclopentylisoquinoline-5-acetonitrile:

1-Cyclopentylisoquinoline (obtained from 1-cyano-2-benzoyl-1,2-dihydroisoquinoline and cyclopentyl bromide) and N-hydroxymethyl dichloroacetamide were reacted in the same way as in step (b) of Example 18 to obtain 1-cyclopentyl-5-dichloroacetylaminomethylisoquinoline having a melting point of 151.0° to 152.3° C. The product was successively reacted in the same way as in steps (c), (d), (e), and (f) of Example 18 to afford 1-cyclopentylisoquinoline-5-acetonitrile having a melting point of 99.4° to 100.0° C.

EXAMPLE 24

Synthesis of 1-cyclopentylisoquinoline-5-acetic acid:

1-Cyclopentylisoquinoline-5-acetonitrile was treated in the same way as in Example 3 to afford 1-cyclopentylisoquinoline-5-acetic acid as colorless prisms having a melting point of 171.7° to 172.5° C.

IR, $\nu_{KBr}{}^{cm-1}$: 3440, 2960, 2440, 1970, 1710, 1205, 818.

NMR, $\delta_{(CD_3)_2SO}{}^{ppm}$: 1.82 (8H, multiplet), 3.98 (1H, multiplet), 4.04 (2H, singlet), 7.63 (3H, multiplet), 8.32 (2H, multiplet).

EXAMPLE 25

Synthesis of 1-sec-butylisoquinoline-5-acetic acid:

1-sec-Butylisoquinoline and N-hydroxymethyl dichloroacetamide were reacted in the same way as in step (b) of Example 18 to afford 1-sec-butyl-5-dichloroacetylaminomethylisoquinoline. The product was reacted successively in the same way as in steps (c), (d), (e) and (f) of Example 18 to obtain 1-sec-butylisoquinoline-5-acetonitrile. The product was treated in the same way as in Example 3 to afford 1-sec-butylisoquinoline-5-acetic acid as an oil.

IR, $\nu_{neat}{}^{cm-1}$: 2900, 2600, 1950, 1720, 1250, 810.

NMR, $\delta_{(CD_3)_2SO}{}^{ppm}$: 0.7 (3H, triplet), 1.3 (3H, doublet), 1.75 (2H, multiplet), 3.7 (1H, multiplet), 4.05 (2H, singlet), 7.5–7.7 (3H, multiplet), 8.2–8.4 (1H, multiplet), 8.45 (1H, doublet).

EXAMPLE 26

Synthesis of 1-ethylisoquinoline-5-acetic acid:

1-Ethylisoquinoline and N-hydroxymethyl dichloroacetamide were reacted in the same way as in step (b) of Example 18 to afford 1-ethyl-5-dichloroacetylaminomethylisoquinoline. The product was reacted successively in the same way as in steps (c), (d), (e) and (f) of Example 18 to afford 1-ethylisoquinoline-5-acetonitrile. The product was treated in the same way as in Example 3 to afford 1-ethylisoquinoline-5-acetic acid having a melting point of 166.2° to 180.8° C.

IR, $\nu_{KBr}{}^{cm-1}$: 3400, 2990, 2400, 1950, 1720, 1320, 1050, 810.

NMR, $\delta_{CDCl_3}{}^{ppm}$: 1.35 (3H, triplet), 3.37 (2H, quartet), 4.1 (2H, singlet), 7.64–7.87 (3H, multiplet), 8.15–8.35 (1H, multiplet), 8.45 (1H, doublet).

EXAMPLE 27

Synthesis of 1-(1-ethylpropyl)isoquinoline-5-acetic acid 1-(1-Ethylpropyl)isoquinoline and N-hydroxymethyl dichloroacetamide were reacted in the same way as in step (b) of Example 18 to afford 1-(1-ethylpropyl)-5-dichloroacetylaminomethylisoquinoline. The product was successively reacted in the same way as in steps (c), (d), (e) and (f) of Example 18 to afford 1-(1-ethylpropyl)-isoquinoline-5-acetonitrile. The product was treated in the same way as in Example 3 to afford 1-(1-ethylpropyl)-isoquinoline-5-acetic acid as an oil. The hydrochloride of the product was in the form of colorless prisms having a melting point of 107° to 109° C.

IR, $\nu_{KBr}{}^{cm-1}$: 2970, 1725, 1640, 1370.

NMR, $\delta_{(CD_3)_2SO}{}^{ppm}$: 0.75 (6H, triplet), 2.10 (4H, multiplet), 4.00 (1H, multiplet), 4.26 (2H, singlet), 8.10 (3H, multiplet), 8.48 (1H, doublet), 8.75 (1H, multiplet).

EXAMPLE 28

Synthesis of 1-isobutylisoquinoline-5-acetonitrile:

1-Amino-2-(2-hydroxymethylphenyl)ethane and isovaleryl chloride were successively reacted in the same way as in steps (b) and (c) of Example 12 to afford 1-isovalerylamino-2-(2-hydroxymethylphenyl)ethane. The product was successively reacted in the same way as in steps (d), (e), (f), and (g) of Example 12 to afford 1-isobutylisoquinoline-5-acetonitrile as an oil.

IR, $\nu_{KBr}{}^{cm-1}$: 2960, 2260, 1620, 1600, 1565, 1500, 815.

NMR, $\delta_{CDCl_3}{}^{ppm}$: 0.99 (6H, doublet), 1.8–2.1 (1H, multiplet), 3.18 (2H, doublet), 4.1 (2H, singlet), 7.2–8.35 (4H, multiplet), 8.05 (1H, doublet).

EXAMPLE 29

Synthesis of 1-isobutylisoquinoline-5-acetic acid:

1-iso-Butylisoquinoline-5-acetonitrile was treated in the same way as in Example 3 to afford 1-isobutylisoquinoline-5-acetic acid having a melting point of 152.1° to 152.5° C.

IR, $\nu_{KBr}{}^{cm-1}$: 3450, 2965, 2460, 1960, 1710, 1620, 1600, 1220, 825.

NMR, $\delta_{(CD_3)_2SO}{}^{ppm}$: 0.95 (6H, doublet), 1.9–2.5 (1H, multiplet), 3.14 (2H, doublet), 3.4 (1H, broad singlet), 4.04 (2H, singlet), 7.5–8.3 (4H, multiplet), 8.42 (1H, doublet).

EXAMPLE 30

Synthesis of 1-n-propylisoquinoline-5-acetonitrile:

1-Amino-2-(2-hydroxymethylphenyl)ethane and butyryl chloride were successively reacted in the same way as in steps (b) and (c) of Example 12 to afford 1-butyrylamino-2-(2-hydroxymethylphenyl)ethane as an oil. The product was successively reacted in the same way as in steps (d), (e), (f) and (g) of Example 12 to afford 1-n-propylisoquinoline-5-acetonitrile.

IR, $\nu_{KBr}{}^{cm-1}$: 2960, 2250, 1618, 1595, 1570, 1500, 810, 750.

NMR, $\delta_{CDCl_3}{}^{ppm}$: 1.05 (3H, triplet), 1.55–2.3 (2H, multiplet), 3.3 (2H, triplet), 4.09 (2H, singlet), 7.2–7.9 (3H, multiplet), 8.17 (1H, double doublet), 8.54 (1H, doublet).

EXAMPLE 32

Synthesis of 1-cyclobutylisoquinoline-5-acetic acid:

1-Amino-2-(2-hydroxymethylphenyl)ethane and cyclobutanecarbonyl chloride were successively reacted in the same way as in steps (b) and (c) of Example 12 to afford 1-cyclobutylcarbonylamino-2-(2-hydroxymethylphenyl)ethane as in oil. The product was successively reacted in the same way as in steps (d), (e), (f) and (g) of Example 12 to afford 1-cyclobutylisoquinoline-5-acetonitrile. The product was treated in the same way as in Example 3 to afford 1-cyclobutylisoquinoline-5-acetic acid having a decomposition point of 202.8° to 209.8° C.

IR, $\nu_{KBr}^{cm-1}$: 2940, 2440, 1940, 1700, 1320, 820.

NMR, $\delta_{(CD_3)_2SO}^{ppm}$: 1.7–2.7 (6H, multiplet), 4.02 (2H, singlet), 4.35 (1H, multiplet), 7.5–8.2 (4H, multiplet), 8.45 (1H, doublet).

EXAMPLE 33

Synthesis of 1-n-hexylisoquinoline-5-acetonitrile:

1-Amino-2-(2-chlorophenyl)ethane and n-heptanoyl chloride were reacted in the same way as in step (a) of Example 13 to afford 1-n-heptanoylamino-2-(2-chlorophenyl)ethane as an oil. The product was successively reacted in the same way as in steps (b), (c), (d), (e), (f), (g) and (h) of Example 13 to afford 1-n-hexylisoquinoline-5-acetonitrile.

IR, $\nu_{KBr}^{cm-1}$: 2950, 2250, 1620, 1600, 1565, 1460, 1410, 1355, 825, 760.

NMR, $\delta_{CDCl_3}^{ppm}$: 0.6–2.2 (11H, multiplet), 3.32 (2H, triplet), 4.09 (2H, singlet), 7.21–8.3 (4H, multiplet), 8.54 (1H, doublet).

EXAMPLE 34

Synthesis of 1-n-hexylisoquinoline-5-acetic acid:

1-n-Hexylisoquinoline-5-acetonitrile was treated in the same way as in Example 3 to afford 1-n-hexylisoquinolin-5-yl acetic acid as colorless needles having a melting point of 152.1° to 152.5° C.

IR, $\nu_{KBr}^{cm-1}$: 3450, 2950, 2400, 1950, 1720, 1620, 1600, 1330, 1080, 840, 755.

NMR, $\delta_{(CD_3)_2SO}^{ppm}$: 0.65–2.0 (11H, multiplet), 3.26 (2H, triplet), 4.02 (2H singlet), 7.5–8.3 (4H, multiplet), 8.38 (1H, doublet).

EXAMPLE 35

Synthesis of 1-tert-butylisoquinoline-5-acetonitrile:

1-Amino-2-(2-methylphenyl)ethane and pivaloyl chloride were reacted in the same way as in step (a) of Example 1 to afford 1-pivaloylamino-2-(2-methylphenyl)-ethane. The product was successively reacted in the same way as in steps (b), (c), (d) and (e) of Example 1 to afford 1-tert-butylsioquinoline-5-acetonitrile.

IR, $\nu_{NaCl}^{cm-1}$: 2980, 2255, 1598, 1500, 1370, 815.

NMR, $\delta_{CDCl_3}^{ppm}$: 1.65 (9H, singlet), 4.09 (2H, singlet), 7.5 (3H, multiplet), 8.53 (1H, doublet), 8.55 (1H, multiplet).

EXAMPLE 36

Synthesis of 1-tert-butylisoquinoline-5-acetic acid:

1-tert-Butylisoquinoline-5-acetonitrile was treated in the same way as in Example 3 to afford 1-tert-butylisoquinoline-5-acetic acid.

IR, $\nu_{KBr}^{cm-1}$: 2980, 1720, 1600, 1370, 816.

NMR, $\delta_{CDCl_3}^{ppm}$: 1.66 (9H, singlet), 3.95 (2H, singlet), 7.48 (3H, multiplet), 8.35 (2H, multiplet), 9.70 (1H, broad singlet).

EXAMPLE 37

Synthesis of 2-(1-isopropylisoquinoline-5-yl)-propionic acid:

(a) 1-iso-Propylisoquinoline-5-acetonitrile was treated in the same way as in step (a) of Example 10 to afford ethyl 2-(1-isopropylisoquinoline-5-yl)-2-cyanopropionate as a colorless oil.

IR, $\nu_{neat}^{cm-1}$: 3970, 2220, 1748, 1237, 818, 758.

NMR, $\delta_{CDCl_3}^{ppm}$: 1.21 (3H, triplet), 1.44 (6H, doublet), 2.23 (3H, singlet), 3.97 (1H, multiplet), 4.26 (2H, quartet), 7.73 (3H, multiplet), 8.44 (1H, multiplet), 8.57 (1H, doublet).

(b) Ethyl 2-(1-isopropylisoquinolin-5-yl)-2-cyanopropionate was treated in the same way as in Example 11 to afford 2-(1-isopropylisoquinolin-5-yl)propionic acid having a melting point of 137.7° to 138.2° C.

IR, $\nu_{neat}^{cm-1}$: 3440, 2970, 1725, 1200, 810, 750.

NMR, $\delta_{CDCl_3}^{ppm}$: 1.48 (6H, doublet), 1.64 (3H, doublet), 3.97 (1H, multiplet), 5.44 (1H, quartet), 7.83 (3H, multiplet), 8.16 (1H, multiplet), 8.61 (1H, doublet).

EXAMPLE 38

Synthesis of 1-(4-methylaminophenyl)isoquinoline-5-acetic acid:

The ethyl 1-(4-aminophenyl)isoquinoline-5-acetate obtained in step (j) of Example 12 was reacted in the same way as in step (k) of Example 12. The resulting oily product was chromatographed. From the 4% ethanolic chloroform eluate, ethyl 1-(4-methylaminophenyl)isoquinoline-5-acetate was obtained. The product was hydrolyzed in the same way as in step (l) of Example 12 to afford 1-(4-methylaminophenyl)isoquinoline-5-acetic acid.

IR, $\nu_{KBr}^{cm-1}$: 3390, 1710, 1610, 820.

NMR, $\delta_{(CD_3)_2SO}^{ppm}$: 2.78 (3H, singlet), 3.35 (1H, broad singlet), 4.08 (2H, singlet), 6.75–8.2 (8H, multiplet), 8.5 (1H, doublet).

EXAMPLE 39

Synthesis of 1-(4-trifluoromethylphenyl)-isoquinoline-5-acetonitrile:

1-Amino-2-(2-hydroxymethylphenyl)ethane and 4-trifluoromethylbenzoyl chloride were successively reacted in the same way as in steps (b) and (c) of Example 12 to afford 1-(4-trifluoromethylbenzoyl)amino-2-(2-hydroxymethylphenyl)ethane having a melting point of 145.8° to 146.3° C. The product was successively reacted in the same way as in steps (d), (e), (f) and (g) of Example 12 to afford 1-(4-trifluoromethylphenyl)isoquinoline-5-acetonitrile having a melting point of 121.9° to 122.6° C.

IR, $\nu_{KBr}^{cm-1}$: 2252, 1330, 1172, 1133, 850, 769.

NMR, $\delta_{CDCl_3}^{ppm}$: 4.18 (2H, singlet), 7.80 (8H multiplet), 8.74 (1H, doublet).

EXAMPLE 40

Synthesis of 1-(4-trifluoromethylphenyl)-isoquinoline-5-acetic acid:

1-(4-Trifluoromethylphenyl)isoquinoline-5-acetonitrile was treated in the same way as in Example 3 to afford 1-(4-trifluoromethylphenyl)isoquinoline-5-acetic acid having a melting point of 228.2° to 229.7° C.

IR, $\nu_{KBr}{}^{cm-1}$: 3440, 2520, 1940, 1718, 1341, 838, 760.

NMR, $\delta_{(CD_3)_2SO}{}^{ppm}$: 4.12 (2H, singlet), 7.88 (8H, multiplet), 8.62 (1H, doublet).

EXAMPLE 41

Synthesis of ethyl 1-isopropylisoquinoline-5-acetate:

1-iso-Propylisoquinoline-5-acetic acid (0.5 g) was dissolved in 20 ml of ethanol, and 3 ml of conc. sulfuric acid was added. The mixture was heated under reflux for 3 hours. The reaction mixture was poured into ice water, made weakly alkaline with potassium carbonate, extracted with benzene, washed in water, and dried. The solvent was distilled off under reduced pressure to afford 0.5 g of ethyl 1-isopropylisoquinoline-5-acetate as a colorless oil.

IR, $\nu_{neat}{}^{cm-1}$: 2970, 1740, 1260, 1175, 1030, 812, 756.

NMR, $\delta_{CDCl_3}{}^{ppm}$: 1.21 (3H, triplet), 1.43 (6H, doublet), 3.96 (1H, multiplet), 4.01 (2H, singlet), 4.14 (2H, quartet), 7.67 (3H, multiplet), 8.17 (1H, multiplet), 8.54 (1H, doublet).

EXAMPLE 42

Synthesis of 1-isopropylisoquinoline-5-acetic acid methylamide:

Ethyl 1-isopropylisoquinoline-5-acetate (0.4 g) was dissolved in 20 ml of ethanol, and 5 ml of a 40% aqueous solution of monomethylamine was added. The mixture was stirred under heat for 12 hours. After the reaction, the solvent was distilled off. The residue was extracted with benzene, washed in water, and dried. The solvent was distilled off under reduced pressure. Recrystallization from benzenecyclohexane afforded 0.15 g of 1-isopropylisoquinoline-5-acetic acid methylamide as colorless needles having a melting point of 153.2° to 153.7° C.

IR, $\nu_{KBr}{}^{cm-1}$: 3290, 2970, 1650, 1572, 816.

NMR, $\delta_{CDCl_3}{}^{ppm}$: 1.44 (6H, doublet), 2.72 (3H, doublet), 3.92 (1H, multiplet), 3.97 (2H, singlet), 5.40 (1H, broad singlet), 7.56 (3H, multiplet), 8.22 (1H multiplet), 8.53 (1H, doublet).

EXAMPLE 43

Synthesis of ethyl 1-phenylisoquinoline-5-acetate:

1-Phenylisoquinoline-5-acetate was treated in the same way as in Example 41 to afford ethyl 1-phenylisoquinoline-5-acetate. Melting point: 141.2°–141.3° C. (hydrochloride).

IR, $\nu_{KBr}{}^{cm-1}$: 1725, 1640, 1380, 1340, 1215, 820.

NMR, $\delta_{(CD_3)_2SO}{}^{ppm}$: 1.22 (3H, triplet), 4.14 (2H, quartet), 4.38 (2H, singlet), 6.9–8.22 (9H, multiplet), 8.38 (1H, doublet), 8.7 (1H, doublet).

EXAMPLE 44

Synthesis of 1-phenylisoquinoline-5-acetamide:

1-Phenylisoquinoline-5-acetic acid (0.7 g) was dissolved in 10 ml of chloroform, and 5 ml of phosphorus oxychloride was added dropwise with stirring at room temperature. The reaction was performed for 2 hours. After the reaction, the solvent was distilled off from the reaction mixture. The residue was dissolved in 5 ml of tetrahydrofuran. Under ice cooling, the solution was added dropwise to ammonia water. The crystals that precipitated were collected by filtration, washed in water, and dried. Recrystallization from ethyl acetate afforded 0.5 g of 1-phenylisoquinoline-5-acetamide having a melting point of 182° C. IR, $\nu_{KBr}{}^{cm-1}$: 3360, 3190, 1665, 1630, 1385.

NMR, $\delta_{CDCl_3}{}^{ppm}$: 3.99 (2H, singlet), 5.5–6.3 (2H, broad singlet), 7.2–8.2 (9H, multiplet), 8.63 (1H, doublet).

EXAMPLE 45

Synthesis of 1-(2-methylphenyl)isoquinoline-5-acetonitrile:

1-Amino-2-(2-chlorophenyl)ethane and o-toluoyl chloride were reacted in the same way as in step (a) of Example 13 to afford 1-(o-toluoylamino)-2-(2-chlorophenyl)ethane having a melting point of 91.6° C. The product was successively reacted in the same way as in steps (b), (c), (d), (e), (f), (g), and (h) of Example 13 to afford 1-(2-methylphenyl)isoquinoline-5-acetonitrile having a melting point of 120.3° to 120.4° C.

IR, $\nu_{KBr}{}^{cm-1}$: 2865, 2245, 1620, 1595, 1565, 1360, 755.

NMR, $\delta_{CDCl_3}{}^{ppm}$: 2.08 (3H, singlet), 4.16 (2H, singlet), 7.2–7.9 (8H, multiplet), 8.73 (1H, singlet).

EXAMPLE 46

Synthesis of 1-(2-methylphenyl)isoquinoline-5-acetic acid:

1-(2-Methylphenyl)isoquinoline-5-acetonitrile was treated in the same way as in Example 3 to afford 1-(2-methylphenyl)isoquinoline-5-acetic acid having a melting point of 191.8° to 192.2° C.

IR, $\nu_{KBr}{}^{cm-1}$: 1695, 1590, 1280, 1255, 810, 750.

NMR, $\delta_{(CD_3)_2SO}{}^{ppm}$: 2.0 (3H, singlet), 4.1 (2H, singlet), 7.1–8.0 (8H, multiplet), 8.6 (1H, doublet).

EXAMPLE 47

Synthesis of 1-(2-chlorophenyl)isoquinoline-5-acetonitrile:

1-Amino-2-(2-methylphenyl)ethane and 2-chlorobenzoyl chloride were reacted in the same way as in step (a) of Example 1 to afford 1-(2-chlorobenzoyl)amino-2-(2-methylphenyl)ethane having a melting point of 90.4° to 90.9° C. The product was successively reacted in the same way as in steps (b), (c), (d) and (e) to afford 1-(2-chlorophenyl)isoquinoline-5-acetonitrile having a melting point of 112.8° to 113.3° C.

IR, $\nu_{KBr}{}^{cm-1}$: 2900, 2245, 1620, 1600, 1360, 815, 760.

NMR, $\delta_{CDCl_3}{}^{ppm}$: 4.13 (2H, singlet), 7.2–7.9 (8H, multiplet), 8.69 (1H, doublet).

EXAMPLE 48

Synthesis of 1-(2-chlorophenyl)isoquinoline-5-acetic acid:

1-(2-Chlorophenyl)isoquinoline-5-acetonitrile was treated in the same way as in Example 3 to afford 1-(2-chlorophenyl)isoquinoline-5-acetic acid having a melting point of 189.5° to 190.2° C.

IR, $\nu_{KBr}{}^{cm-1}$: 1710, 1620, 1600, 1440, 1270, 1040, 825, 770.

NMR, $\delta_{(CD_3)_2SO}{}^{ppm}$: 4.12 (2H, singlet), 7.4–8.0 (8H, multiplet), 8.1 (1H, doublet).

Examples of the production of pharmaceutical preparations containing the compound of the present invention are given below.

EXAMPLE A

Tablets:

Tablets each containing 10 mg or 25 mg of the active compound are prepared as follows:

| | mg/tablet |
|---|---|
| Prescription 1-a (10 mg tablet) | |
| 1-(4-Dimethylaminophenyl)iso-quinoline-5-acetic acid | 10 |
| Lactose | 132.2 |
| Starch | 44.8 |
| Calcium carboxymethyl cellulose | 10 |
| Talc | 2 |
| Magnesium stearate | 1 |
| | 200.0 mg |
| Prescription 1-b (25 mg tablet) | |
| 1-(4-Dimethylaminophenyl)isoquinoline-5-acetic acid | 25 |
| Lactose | 117.2 |
| Starch | 44.8 |
| Calcium carboxymethyl cellulose | 10 |
| Talc | 2 |
| Magnesium stearate | 1 |
| | 200.0 mg |

Crystals 1-(4-dimethylaminophenyl)isoquinoline-5-acetic acid are pulverized to less than 70 microns, and lactose and starch are added, followed by thorough mixing. A 10% starch paste was added to the mixed powder, and they were mixed with stirring to prepare granules. After dry granulation, the particle size of the granules was maintained uniform at about 840 microns. Talc and magnesium stearate were mixed with the granules, and tablets were prduced from the granules.

EXAMPLE B

| Capsules: Prescription 2 (25 mg capsule) | |
|---|---|
| | mg/capsule |
| 1-(4-Dimethylaminophenyl)iso-quinoline-5-acetic acid | 25 |
| Starch | 42 |
| Lactose | 40 |
| Magnesium stearate | 3 |
| | 110 mg |

1-(4-Dimethylaminophenyl)isoquinoline-5-acetic acid was finely pulverized, and starch, lactose and magnesium stearate was added to the pulverized product. They were mixed well, and the mixture was filled into No. 5 capsules.

Example C

| Suppository: Prescription 3 (50 mg suppository) | |
|---|---|
| | mg/suppository |
| 1-(4-dimethylaminophenyl)iso-quinoline-5-acetic acid | 50 |
| Macrogol 1000 | 1463 |
| Macrogol 4000 | 487 |
| | 2000 mg |

1-(4-Dimethylaminophenyl)isoquinoline-5-acetic acid was well pulverized, and Macrogol 1000 (polyethylene glycol having an average molecular weight of about 1000) and Macrogol 4000 (polyethylene glycol having an average molecular weight of about 4000) were added. They were well mixed, and then melted. The molten mixture was cast into a mold for a suppository, colled to solidify it, and then taken out.

What we claim is:

1. A compound of the formula

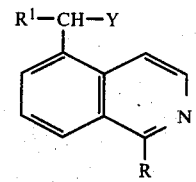

wherein R represents isopropyl, cyclopentyl, cyclohexyl, or a group of the formula

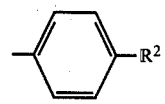

in which $R^2$ represents hydrogen, halogen, methyl, trifluoromethyl, methoxy, methylamino or dimethylamino; $R^1$ represents hydrogen or alkyl of up to 6 carbon atoms; and Y represents carboxyl and alkoxycarbonyl of up to 6 carbon atoms in the alkoxy group; or a salt thereof.

2. A compound of claim 1 wherein $R^2$ represents hydrogen, chlorine, bromine, fluorine, methyl or dimethylamino.

3. A compound of claim 2 or 1 wherein $R^1$ represents hydrogen or methyl.

4. A compound of claim 2 or 1 wherein Y represents carboxyl.

5. A compound of claim 1 which is 1-(4-chlorophenyl) isoquinoline-5-acetic acid, 1-(4-bromophenyl)-isoquinoline-5-acetic acid, 1-(4-methylphenyl) isoquinoline-5-acetic acid, 1-(4-dimethylaminophenyl) isoquinoline-5-acetic acid, or 1-cyclohexylisoquinoline-5-acetic acid.

6. A compound according to claim 1 in which Y represents alkoxycarbonyl of up to 6 carbon atoms in the alkoxy group.

7. A compound according to claim 1 in which Y is a carboxyl group, $R_1$ is hydrogen, and R represents a group of the formula

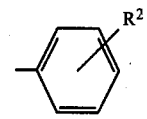

wherein $R^2$ is hydrogen.

8. A pharmaceutical composition having anti-inflammatory or analgesic activity which comprises (1) an effective amount of compound of the formula

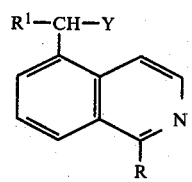

wherein R represents isopropyl, cyclopentyl, cyclohexyl, or a group of the formula

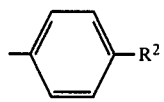

in which R² represents hydrogen, halogen, methyl, trifluoromethyl, methoxy, methylamino or dimethylamino; R¹ represents hydrogen or alkyl of up to 6 carbon atoms; and Y represents carboxyl and alkoxycarbonyl of up to 6 carbon atoms in the alkoxy group;

or its pharmaceutically acceptable salt, and (2) a pharmaceutically acceptable diluent or carrier.

9. A composition according to claim 8 wherein the Y group in the compound is a carboxyl group.

10. A composition according to claim 8 wherein the Y group in the compound is an alkoxycarbonyl of up to 6 carbon atoms in the alkoxy group.

* * * * *